US008574865B2

(12) United States Patent
Wright et al.

(10) Patent No.: US 8,574,865 B2
(45) Date of Patent: Nov. 5, 2013

(54) METHODS AND ASSAYS FOR IDENTIFYING COMPOUNDS THAT MODULATE PROTEIN-PROTEIN INTERACTIONS

(75) Inventors: Paul Steven Wright, New Hope, PA (US); Paul Weissensee, Andover, NJ (US); Haifeng Eishingdrelo, Montville, NJ (US); Jidong Cai, Bedminster, NJ (US)

(73) Assignee: Sanofi, Paris (FR)

( * ) Notice: Subject to any disclaimer, the term of this patent is extended or adjusted under 35 U.S.C. 154(b) by 388 days.

(21) Appl. No.: 12/676,284

(22) PCT Filed: Aug. 28, 2008

(86) PCT No.: PCT/US2008/074543
§ 371 (c)(1),
(2), (4) Date: May 20, 2010

(87) PCT Pub. No.: WO2009/032716
PCT Pub. Date: Mar. 12, 2009

(65) Prior Publication Data
US 2010/0311096 A1    Dec. 9, 2010

Related U.S. Application Data

(60) Provisional application No. 60/969,756, filed on Sep. 4, 2007, provisional application No. 61/084,987, filed on Jul. 30, 2008.

(51) Int. Cl.
*C12Q 1/37* (2006.01)

(52) U.S. Cl.
USPC .......................................................... 435/23

(58) Field of Classification Search
USPC .......................................................... 435/23
See application file for complete search history.

(56) References Cited

U.S. PATENT DOCUMENTS

| | | | |
|---|---|---|---|
| 5,891,646 | A | 4/1999 | Barak et al. |
| 6,110,693 | A | 8/2000 | Barak et al. |
| 6,528,271 | B1 | 3/2003 | Bohn et al. |
| 6,884,870 | B2 | 4/2005 | Hav et al. |
| 7,049,076 | B2 | 5/2006 | Lee et al. |
| 7,128,915 | B2 | 10/2006 | Hernandez et al. |
| 2003/0143626 | A1 | 7/2003 | Colas et al. |
| 2003/0157553 | A1 | 8/2003 | Berstein |
| 2004/0002119 | A1 | 1/2004 | Iannone et al. |
| 2005/0100934 | A1* | 5/2005 | Lee et al. ............. 435/6 |
| 2006/0115871 | A1 | 6/2006 | Bruce |
| 2007/0224615 | A1* | 9/2007 | Lee et al. ............. 435/6 |
| 2011/0283373 | A1* | 11/2011 | Binkowski et al. ...... 800/13 |

OTHER PUBLICATIONS

Zozulya et al., The human olfactorty receptor repertoire, Genome Biology. vol. 2, No. 6, 2001, pp. 0018.1-0018.12.

Azzi et al., Beta-Arrestin-mediated activation of MAPK by inverse agonists reveals distinct active conformations for G protein-coupled receptors, PNAS, vol. 100, No. 20, Sep. 30, 2003, pp. 11406-11411.
Defea, K., Beta-Arrestins and heterotrimeric G-proteins: collaborations and competitors in signal transduction, Br. J. of Pharmacology, vol. 153, 2008, pp. S298-S390.
Feilmeier et al., Green Fluorescent Protein Functions as a Reporter for Protein Localization in *Escherichia coli*, J. of Bacteriology. vol. 182, No. 14, Jul. 2000, pp. 4068-4076.
Ferguson, S., Evolving Concepts in G Protein-Coupled Receptor Endocytosis: The Role in Receptor Desensitization and Signaling, Pharmacology Review, vol. 53, No. 1, 2001, pp. 1-24.
Fredriksson et al., The G-Protein-Coupled Receptors in the Human Genome Form Five Main Families. Phylogenetic Analysis, Paralogon Groups, and Fingerprints, Molecular Pharmacology, vol. 63, No. 6. 2003, pp. 1256-1271.
Ghosh et al., Antiparallel Leucine Zipper-Directed Protein Reassembly: Appliction to the Green Fluorescent Protein, J. of the Am. Chem. Soc., vol. 122, No. 23, Jun. 14, 2000, pp. 5658-5659.
Glusman et al., The Complete Human Olfactory Subgenome, Genome Res. vol. 11, 2001, pp. 685-702.
Howard et al., Orphan G-protein-coupled receptors and natural ligand discovery, Trends in Pharmacol. Sci. vol. 22, No. 3, Mar. 2001, pp. 132-140.
Hu et al., Visualization of interactions among bZIP and Re1 family proteins in living cells using biomolecular fluorescence complementation, Molecular Cell, vol. 9, No. 4, Apr. 1, 2002, pp. 789-798.
Kapust et al., The Pl' specifity of tobacco etch virus protease, Biochem. & Biophy. Res. Comm., vol. 294, 2002. pp. 948-955.
Kovoor et al., Targeted Construction of Phosphorylation-independent Beta-Arrestin Mutants with Constitutive Activity in Cells, J. of Biol. Chem, vol. 274, No. 11, Mar. 12, 1999, pp. 6831-6834.
Luttrell et al., The role of Beta-arrestins in the termination and transduction of G-protein-coupled receptor signals, J. of Cell Science, vol. 115, 2002, pp. 455-465.
Oakley et al., Association of Beta-Arrestin with G Protein-coupled Receptors during Ciathrin-mediated Endocytosis Dictates the Profile of Receptor Resensitization, J. of Biol. Chem., vol. 274, No. 45, Nov. 5, 1999, pp. 32248-32257.
Oakley et al., Molecular Determinants Underlying the Formation of Stable Intracellular G Protein-coupled Receptor-Beta-Arresin Complexes after Receptor Endocytosis, J. of Biol. Chem., Vo.276, No. 22, Jun. 1, 2001, pp. 19452-19460.
Oakley et al., The Cellular Distribution of Fluorescently Labeled Arrestins Provides a Robust, Sensitive, and Universal Assay for Screening G Protein-Coupled Receptors, Assay and Drug Development Technologies, vol. 1, No. 1-1, 2002, pp. 21-29.
Ozawa et al., Designing split reporter proteins for analytical tools, Analytica Chimica ACTA, vol. 556, No. 1, Jan. 18, 2006, pp. 58-68.
Paulmurugan et al., Noninvasive imaging of protein-protein interactions in living subjects by using reporter protein complementation and reconstitution strategies, PNAS, vol. 99, No. 24, Nov. 26, 2002, pp. 15606-15613.

(Continued)

*Primary Examiner* — Ralph Gitomer
(74) *Attorney, Agent, or Firm* — Lathrop & Gage LLP; James H. Velema, Esq.

(57) ABSTRACT

Methods and assays for identifying a compound that modulates a protein-protein interaction between a first and a second protein. The methods and assays require a protease that is attached to the second protein and a split and rearranged reporter activating protein that is attached to the first protein, wherein the reporter activating protein comprises a cleavage site for the protease that is interposed between two portions of the reporter activating protein and wherein the two portions of the reporter activating protein are in a rearranged order.

26 Claims, 17 Drawing Sheets

(56) References Cited

OTHER PUBLICATIONS

Piehler et al., New methodologies for measuring protein interactions in vivo and in vitro, Current Opinion in Structural Biology, vol. 15, No. 1, Feb. 1, 2005, pp. 4-14.

Stagler et al., A genetic system based on split-uniquitin for the analysis of interactions between membrane proteins in vivo, PNAS, vol. 95, Apr. 1, 1998, pp. 5187-5192.

Takeda et al., Identification of G protein-coupled receptor genes from the human genome sequence, FEBS Letters, vol. 520, 2002, pp. 97-101.

Vassilatis et al., The G protein-coupled receptor repertoires of human and mouse, PNAS, vol. 100, No. 8, Apr. 15, 2003, pp. 4903-4908.

Violin et al., Beta-Arrestin-biased ligands at seven-transmembrane receptors, Trends in Pharmacol. Sci., vol. 26, No. 8, 2007, pp. 416-422.

Wehr et al., Monitoring Regulated Protein-Protein Interactions Using Split TEV, Nature Methods, vol. 3, No. 12, Dec. 1, 2006, pp. 985-993.

Wehrman et al., Protein-protein interactions monitored in mammalian cells via complementation of beta-lactamase enzyme fragments, PNAS, vol. 99, No. 6, Mar. 19, 2002. pp. 3469-3474.

International Search Report WO2009/032716A1 dated Mar. 12, 2009.

Eishingdrelo et al., Current Chemical Genomics, vol. 5, pp. 1-7 (2011).

Notice of Allowance for Canadian Patent Application No. 2,698,362, Jul. 2012.

Notice of Allowance for Russian Patent Application No. 2010112854.

Written Opinion from PCT Application No. PCT/US2008/074543, dated Jan. 22, 2009.

Office Action for Canadian Patent Application No. 2,698,362, dated Nov. 28, 2011.

Office Action for Chilean Patent Application No. 2008-002602, dated Oct. 4, 2011.

Office Action for Mexican Patent Application No. MX/a/2010/002399, dated Nov. 7, 2011.

Office Action for Russian Patent Application No. 2010112854, dated Jun. 5, 2012.

PNAS, 2002, vol. 99, No. 24, 15608-15613.

* cited by examiner

METHODS AND ASSAYS FOR IDENTIFYING COMPOUNDS THAT MODULATE PROTEIN-PROTEIN INTERACTIONS

This application is a National Stage application filed under Rule 371 based upon PCT/US08/74543 filed Aug. 23, 2008, which claims benefit of priority to US provisional application 61/084,987 filed Jul. 30, 2008, which claims benefit of priority to US provisional application 60/969,756 filed Sep. 4, 2007.

FIELD OF THE INVENTION

This invention relates to materials and methods for determining interaction between molecules of interest. More particularly, it relates to determining if a particular substance, e.g., a "test compound," modulates the interaction of two or more specific proteins of interest. Determination involves monitoring activation of a reporter gene which can be in a cell, in solution or in an artificial package or unit containing one or more reactants of interest, where the activation or lack thereof, results from modulation or lack of modulation. The determination generally occurs using transformed or transfected cells, also featured as an aspect of the invention, as are the agents used to transform or transfect them. A cell-free system or a system using an artificial package or unit carrying one or more reagents of interest, such as a virus, a virus-like particle, a liposome and the like, may also be employed.

BACKGROUND AND RELATED ART

The study of protein/protein interaction, as exemplified, e.g., by the identification of ligands for receptors, is an area of great interest. Even when a ligand or ligands for a given receptor are known, there is interest in identifying more effective or more selective ligands. G-protein coupled receptors, GPCRs, also known as seven transmembrane receptors (7TMR), will be discussed herein as a non-exclusive example of a class of proteins which can be characterized in this way. However, any proteins that interact, for example, members of a metabolic pathway or a cascade, are suitable for use with the instant assay.

GPCRs are the largest class of cell surface receptors known for humans and thus are considered a prime application of the invention. Ligands that modulate signaling by GPCRs include hormones, neurotransmitters, peptides, glycoproteins, lipids, nucleotides, and ions. GPCRs also are known to be sense receptors, e.g., receptors for light, odor, a pheromone, and taste. Given these diverse and numerous roles, GPCRs are the subject of intense research, for example, for chemical defense and bio-defense applications and for drugs useful in treating various conditions. Many drug discovery successes have already occurred. For example, Howard, et al., *Trends Pharmacol. Sci.*, 22:132 140 (2001) has estimated that over 50% of marketed drugs act on such receptors.

"GPCRs" as used herein, refer to any member of the GPCR superfamily of receptors. This superfamily is characterized by a seven-transmembrane domain (7TM) structure. Examples of these receptors include, but are not limited to, the class A or "rhodopsin-like" receptors; the class B or "secretin-like" receptors; the class C or "metabotropic glutamate-like" receptors; the Frizzled and Smoothened-related receptors; the adhesion receptor family or EGF-7TM/LNB-7TM receptors; adiponectin receptors and related receptors; and chemosensory receptors including odorant, taste, vomeronasal and pheromone receptors. As examples, the GPCR superfamily in humans includes, but is not limited to, receptor molecules described by Vassilatis, et al., *Proc. Natl. Acad. Sci. USA*, 100:4903 4908 (2003); Takeda, et al., *FEBS Letters*, 520:97 101 (2002); Fredricksson, et al., *Mol. Pharmacol.*, 63:1256 1272 (2003); Glusman, et al., *Genome Res.*, 11:685 702 (2001); and Zozulya, et al., *Genome Biol.*, 2:0018.1 0018.12 (2001).

In brief, the general mechanism of action of GPCR function is as follows: 1) a GPCR binds a ligand 2) causing a conformational change thereby 3) stimulating a cascade of cellular events that lead to a change in cell physiology. GPCRs transduce signals by modulating activity of a plurality of intracellular proteins, such as, heterotrimeric guanine nucleotide binding proteins (G proteins) and β arrestins. In the case of G proteins, the ligand-receptor complex stimulates guanine nucleotide exchange and dissociation of the G protein heterotrimer into α and βγ subunits. In other circumstances, a β arrestin can substitute for a G protein, oppose G protein signaling, synergize G protein signaling and so on.

Both the GTP-bound α subunit and the βγ heterodimer have been observed to regulate various cellular effector proteins, including adenylyl cyclase and phospholipase C (PLC). In conventional cell-based assays for GPCRs, receptor activity is monitored by measuring the output of a G protein-regulated effector pathway, such as, accumulation of cAMP, produced by adenylyl cyclase; or release of intracellular calcium, e.g., stimulated by PLC activity.

Conventional G protein-based signal transduction assays have been difficult to develop for some targets for a variety of reasons. For example, first, different GPCRs are coupled to different G protein-regulated signal transduction pathways. Traditional G protein-based assays are dependent on knowing the G protein specificity of the target receptor, or the assays require engineering of the cellular system to force couple the target receptor to a selected G protein effector pathway. Second, since the GPCR superfamily is so large, all cells express many endogenous GPCRs (as well as other receptors and signaling factors). Thus, the measured effector pathways can be modulated by endogenous molecules in addition to the target GPCR. This phenomenon can cause false positive or false negative results, e.g., when attempting to identify selective modulators of a target GPCR.

Regulation of G protein activity is not the only result of ligand/GPCR binding. See, for example, Luttrell, et al., *J. Cell Sci.*, 115:455 465 (2002), and Ferguson, *Pharmacol. Rev.*, 53:1 24 (2001), which review activities that can lead to attenuation or termination of the GPCR signal. These termination processes are useful to prevent excessive cell stimulation, and to enforce a temporal linkage between an extracellular signal and the corresponding intracellular pathway.

In general, binding of an agonist to a GPCR causes serine and threonine residues at the C terminus of the receptor molecule to be phosphorylated by GPCR kinase. Agonist-complexed C terminal-phosphorylated GPCRs then interact with arrestin family members, e.g., α arrestin, β arrestin or β arrestin 2, which down modulate or arrest receptor signaling. The binding can inhibit coupling of the receptor to G proteins, thereby targeting the receptor for internalization, followed by degradation and/or recycling. For example, binding of an arrestin, such as β arrestin 2 to a phosphorylated GPCR can reduce activity of the target GPCR in different ways. The simplest mechanism for an arrestin to inhibit activation of its target is to bind to the intracellular domain of the GPCR thereby blocking the binding site for the heterotrimeric G protein and preventing extracellular signals from activating the pathway (desensitization). Another regulatory mechanism employed by arrestins is linkage of the receptor to elements of the membrane internalization machinery (e.g., clathrin-mediated endocytosis) which initiates internalization of the receptor in a coated vesicle for fusion with an endosome. Once at an endosome, the receptor can be either targeted for degradation (e.g., by lysosomes) or can be recycled to the plasma membrane where it can once again be activated.

Hence, the binding of a ligand to a GPCR can be said to "modulate" the interaction between the GPCR and arrestin proteins, since the binding of ligand to GPCR causes the arrestin to bind to the GPCR, thereby modulating its activity. Herein, when "modulates" or any form thereof is used with respect to interaction or binding, it refers simply to some change in the way the two proteins of the invention interact, when, for example, a test compound or ligand is present, as compared to how these two proteins interact, in its absence. Hence, modulate includes mere binding of two molecules. For example, the presence of the test compound may strengthen or enhance the interaction of the two proteins, weaken it, block it, inhibit it, redirect it, lessen it or modify it in some way, manner or form which is detectable, or the test compound may facilitate the likelihood of interaction and so on.

In some circumstances, 7TMR signaling can occur independent of G proteins. Thus, on 7TMR binding of ligand, β arrestin instead of G protein is recruited to precipitate or to initiate a signaling cascade in the cell. See, for example, Violin & Lefkowitz, *Trends Pharm Sciences* 28 (8) 416-422, 2007 and DeFea, *Br J Pharm* 1-12, doi:10.1038/sj.bjp.0707508, 2007 who summarize the two independent and interdependent signaling pathways beginning at the activated 7TMR, and which can involve both a G protein and a β arrestin; or involve either a G protein or a β arrestin.

Thus, for example, known antagonists of a 7TMR activate β arrestin signaling. Propranolol, a known antagonist of the $β_2$ adrenergic receptor (ADRB2) and of G protein signaling, was found to be a partial agonist of β arrestin signaling, activating β arrestin-initiated pathways, as observed practicing the instant invention.

Cell signaling events responsive to extracellular stimuli are generally mediated by protein-protein interactions. Protein-protein interactions therefore are of great interest to cell physiologists. One tool to monitor these interactions involves using a split or permuted reporter activating protein, such as, tobacco etch virus (TEV) protease. The split portions of the protease regain activity when co-expressed as a fusion construct with interacting proteins. Wehr, et al., "Monitoring Regulated Protein-protein Interactions Using Split TEV", *Nature Methods,* 3:985-993 (2006). This property has been used in conjunction with transcription-coupled reporter systems.

This understanding has led to alternate methods for assaying activation and inhibition of GPCRs. One of these methods involves monitoring interaction with arrestins in an intact cell carrying transcription machinery. An advantage of this approach is that no knowledge of G protein pathways is necessary. See, e.g., U.S. Pat. No. 7,049,076: "Method for Assaying Protein-Protein Interaction" to Lee at al. Lee et al. teach a reporter system that requires transcription-coupled reporter systems. According to Lee et al., a peptidic transcription factor is cleaved from a first protein when two proteins interact. The second protein is a transcription factor that activates a reporter gene. The factor then accomplishes the reporter function by transport to the nucleus to effect transcription of a detectable reporter. Because the method is dependent on transcription, the method is inoperable, for example, in platelets, artificial packages or units, such as liposomes, cochleates, virus-like particles, and viral particles.

Oakley, et al., *Assay Drug Dev. Technol.,* 1:21 30 (2002) and U.S. Pat. Nos. 5,891,646 and 6,110,693, "Methods Of Assaying Receptor Activity and Constructs Useful in Such Methods" to Barak et al., describe assays where the redistribution of fluorescently-labeled arrestin molecules in the cytoplasm to activated receptors on the cell surface is measured. These methods rely on high resolution imaging of cells to measure arrestin relocalization and receptor activation. It is recognized by the skilled artisan that this is a complex, involved procedure that can be waylaid by the affinity and interaction of the complementary enzyme fragments used therein which can compete with the desired modulator-induced interaction. Hence, the method suffers from false positives arising from an auto-reassociation of the enzyme, independent of ligand binding. A simpler, more robust assay with a lower incidence of false positives, and which is more readily adaptable to high throughput screening would be desirable.

Various other US patents and patent applications dealing with these points have issued and have been filed. For example, U.S. Pat. No. 6,528,271, "Inhibition Of β-Arrestin Mediated Effects Prolongs and Potentiates Opioid Receptor-Mediated Analgesia" to Bohn et al., features assays to screen for pain-controlling medications, where inhibition of β arrestin binding is measured. Published U.S. patent applications, such as 2004/0002119, 2003/0157553 and 2003/0143626; and U.S. Pat. No. 6,884,870, describe different forms of assays involving GPCRs. U.S. Pat. No. 7,128,915 features similar GPCR technology. U.S. Pat. No. 7,049,076 mentioned above generally featuring GPCR activities or screening assays demonstrate the importance of GPCR research.

Thus, one feature of the present invention, i.e., providing a simpler assay for monitoring and/or determining modulation of specific protein/protein interactions, for example, receptor-mediated physiology, such as GPCR-mediated cellular responses, where the proteins include, but are not limited to, membrane-bound proteins, including receptors in general, and GPCRs as an important example, is satisfactory for addressing a desired need in the art.

SUMMARY OF THE INVENTION

The present invention provides methods to determine if a test compound modulates a specific protein-protein interaction of interest. Protein-protein interaction is a common mechanism of biology whereby a cell can interact with its surroundings, an extracellular event, such as, a ligand binding to a receptor, and can produce an internal response with or without internalization of the ligand. Internalization may involve two or more proteins with portions on or outside the membrane. Thus, dimer, heterodimer or multimer formation can produce an internal response. Intracellular protein-protein interactions also can be involved in signaling cascades. A general scheme of the present invention is applicable to protein-protein interactions of any type. The interaction may, for example, be between two membrane-bound proteins, between a membrane-bound protein and a cytoplasmic protein, between cytoplasmic proteins, etc. One embodiment features a cytoplasmic protein that translocates to another organelle, such as a nucleus, where a reporter is activated to produce a signal. Preferably a cell-based assay is used, but a cell-free system, for example, using lysates, membrane fractions, nuclear fractions, etc., can be used. Included are artificial packages or units containing one or more reagents of interest, such as liposomes, virus-like particles and so on.

The present invention improves on Lee et al. discussed above in that no transcription is necessary. Results can thus be more rapidly obtained and can be obtained from cell-based or cell-free systems. A general description of some especially preferred embodiments appears below. These embodiments are merely illustrative and by no means limit the breadth of the invention described and claimed herein.

One feature provided by the present invention comprises contacting at least one test compound with a cell surface that expresses a protein of interest. The test compound can be assessed for its ability to modulate activity of the protein of interest, e.g., a receptor protein. Expression of the protein of interest in a cell may result from transformation or transfection of a selected cell, e.g., of an insect or mammalian cell line, with: (1) a nucleic acid molecule or molecules which comprise(s), (a) a polynucleotide which encodes a first protein of interest, and (b) a polynucleotide encoding a reporter activating protein configured with a cleavage site sensitive to a protease or an active or activatable portion of a protease, and (2) a nucleic acid molecule or molecules which comprise(s), (a) a polynucleotide which encodes a second protein whose interaction with the first protein of interest changes when a modulator, e.g., a positive test compound, is present, and (b) a polynucleotide that encodes a protease or an active or activatable portion of a protease that is specific for the cleavage site encoded by nucleic acid (1). Molecules, e.g., a positive test compound, that modulate a protein-protein interaction of interest (between the two proteins of interest) can be assessed or assayed by adding, for example, when needed, substrates of reporter activating protein in cells expressing the first and second proteins of interest and a reporter system as described herein.

Thus, a method resulting from the present invention can be use of a permutable enzyme as readout for a protein-protein interaction of interest. The permutable activating protein, such as, an enzyme, used as a reporter or reporter activating protein may be in an inactive state that can be activated by cleavage, for example, by enzymatic activity associated with the second protein of interest. Another option comprises an inactive reporter activating protein that is activated when the first and second proteins of interest interact. Thus, compounds that modulate interaction of the first and second proteins of interest can be screened. One accomplishment of this system permits high throughput identification of molecules that modulate selected protein-protein interactions.

An enzyme capable (alone or with one or more associated molecules) of producing a readout "peptide A" is present in a form whose activity can be changed. The enzyme can be either activated or inactivated by this change. For example, a cleavage site may be built into the enzyme to inactivate it upon cleavage, for example, by a second enzyme coupled with the second protein of interest.

Alternatively cleavage may result in activation. The enzyme(s) of choice may be engineered into a desired host cell using one or more nucleic acids. For example, a vector may comprise a polynucleotide that encodes a selected molecule as an inactive enzyme that can be activated by cleaving the inactive enzyme at a cleavage site. The cleavage site may be naturally occurring, but preferably the cleavage site is engineered into the polynucleotide so that it is expressed as a permuted enzyme. For example, a cleavage site not native to the protein of that cell and/or a protein not native to the host cell can be transfected into the host cell. Alternative embodiments include an enzyme activated by cleavage either by removing a blocking peptide or by allowing two polypeptides to change configuration so that they rearrange to activate enzymatic activity.

Thus, one embodiment features an active polypeptide, for example an enzyme. The "enzyme" may be inactivated by cleavage. For specificity, it may be desirous to engineer a cleavage site into the enzyme recognized by a protease that is not native to the host cell. The cleavage site may be introduced in the form of a linker that binds, i.e., holds in contact, two portions or motifs of the "enzyme", the linker may be a cleavage site native to the "enzyme", for example, the enzyme with a cleavage site may be from another cell type or another species and not found in the host cell, or the cleavage site may be produced by conservative substitution of one or more amino acids. Conservative substitutions are as known in the art. For example charge, size, aromaticity or other traits may be conserved to maintain activity. The activity need not be identical to the non-permuted "enzyme", but must be altered by cleavage at the cleavage site. A cleavage site may be interposed between two portions of an enzyme. Cleaving this site may disrupt the enzyme thus causing inactivation or may allow catalytic activity to occur, e.g., by removing a peptide portion that blocks a binding or catalytic site or by allowing two portions of a permuted enzyme to interact in a manner that restores activity.

Thus, cleavage at the cleavage site can inactivate or activate the protein that produces a readout. Cleavage may be accomplished in the presence of a test compound, for example, when an expression product of a nucleic acid molecule that comprises a polynucleotide encoding the second protein of interest interacts with the first protein of interest thereby initiating activity of a protease that recognizes and cleaves the protease sensitive cleavage sequence in the permuted reporter activating protein.

A second protein of interest interacts with the first protein of interest in the presence of, or alternatively in the absence of, a third molecule. This third molecule is thus said to modulate protein-protein interaction between polypeptides A and B. Protein-protein or peptide-peptide interaction (for purposes of discussion protein and peptide are used interchangeably) that is modulated by a third molecule, e.g., a test compound, is thus efficiently reported by the system of the present invention. Molecules that modulate protein-protein interaction (between polypeptides designated 1 and 2, first and second, A and B, and so, which phrases and terms are used interchangeably herein) can be measured by the active reporter activating molecule or by adding a substrate of the active reporter activating protein to cells expressing the system comprising the proteins of interest.

The selection of proteins A and B is a design choice as pairs of molecules known or suspected to associate, interact and so on can be used. As discussed herein, a suitable pair is a 7TMR with either a G protein or a β arrestin. Another example is a frizzled receptor and a Dishevelled binding protein; and so on. Yet another example would be one which operates during and after cell-cell interaction. Hence, proteins A and B are in cell 1. When cell 1 is contacted by or with cell 2, that interaction triggers an action by and in cell 1 revealed by proteins A and B associating, interacting and so on, and further revealed by the reagents of the instant invention yielding a discernable and detectable signal.

Yet another example is for protein A to be expressed on cell 1 and for protein B to be expressed on cell 2. That can be accomplished, for example, by engineering a G protein or a β arrestin to have an extracellular domain, or by engineering a reporter activating protein to have an extracellular domain that is acted on, for example, by or with cell 1 following activation of cell 1 with a ligand or drug candidate. Alternatively, endogenous molecules on the two cells may spontaneously associate. In another embodiment, the protease and the reporter activating molecule are configured to be expressed on the surface of a cell or unit, as extracellular domains.

In yet another embodiment, proteins that associate, assemble and so on to form a composite structure comprise proteins A and B. The instant assay can be used to identify molecules that facilitate or prevent association or assembly. An example would be the formation of a virus capsid, virus-like particle assembly or ribosome formation.

In common mechanisms of G protein-coupled receptors (GPCRs also known as 7TMRs, which terms are used herein interchangeably), agonist activation of the GPCR results in recruitment of an intracellular molecule which is involved in a signaling pathway, such as initiating, terminating, synergizing, opposing and so on, such as a G protein or a β arrestin. Thus, a G protein-coupled receptor kinase can act on the activated receptor resulting in phosphorylation of the receptor. The phosphorylated receptor facilitates β arrestins binding to the receptor. This mechanism is well conserved for some GPCRs. In other circumstances, the activated receptor interacts instead with a β arrestin.

To assess molecules modulating protein-protein interaction, such as GPCR activation, a system was designed to assay protein-protein interactions and tested in a GPCR-permuted reporter molecule system. For example, the reporter molecule system can be a luciferase/luciferin assay system. Generally, the reporter molecule is an exogenous molecule foreign to the host cell or signaling mechanism. That minimizes spontaneous activation of the reporter molecule by and in the host cell and thus, signal generation, and hence, false positives. The reporter activating molecule can be one with a domain structure or one which can be permuted to yield an inactive reporter activating protein which has the potential of reporter activity when manipulated. Hence, the instant application contemplates the use of a latent reporter activating molecule. The permuted reporter activating molecule minimizes spontaneous reporter activating molecule activity, and hence false positives. For example, in enzyme fragment complementation assays, the affinity of the enzyme fragments can override reaction kinetics with the target molecule, ligand or molecule being screened so that spontaneous reassociation of the enzyme fragments into a functional molecule occurs, thereby contributing to higher background and/or false positives. The permuted reporter activating protein of interest can be engineered to carry a site which when acted on, enables the permuted reporter activating molecule to form a functional molecule. That site can be a protease site. The protease site preferably is one which is a unique site rarely present or not present in the host cell or unit in which the component or components of the method of interest reside. That provides another means to avoid spontaneous reassociation of intact reporter activating molecule, and hence minimizes false positives. Specific signal is obtained only if engaged ligands ultimately induce the protease into proximity with the inactive reporter activating protein to cleave same, and only at that point can an active signal activating or generating entity be realized. There are a number of proteases known in the art which can be used in the practice of the instant invention. For example, proteases from viral sources can be useful as those generally are foreign to an intact host cell. One application comprises a permuted reporter activating protein gene wherein the coding sequence for firefly luciferase is tagged onto or with the C terminal end of a GPCR sequence, and β arrestin 2 (Ar2 or Arr2) is linked to the tobacco etch virus (TEV) protease gene. In another embodiment, a permuted luciferase is tagged to a β arrestin (Ar or Arr) and a TEV gene is linked to a downstream protein of a signaling pathway acted on or involved with β arrestin, or to a receptor such as a 7TMR suspected of acting independent of G proteins. When plasmids engineered to express both of the above are expressed in cells, compounds modulating GPCR-arrestin-2 interaction, recruit the Arr2-protease fusion protein to the protease recognition site in the permuted luciferase and the TEV protease cleaves the permuted luciferase. Effects of the test compounds can be measured through the change in enzyme activity brought about by reconstitution of the reporter activating protein, in this case, the luciferase becomes active and can generate a detectable signal by acting on a suitable substrate, such as a luciferin.

The invention is not limited to luciferase or even to enzymes. Activation by cleavage is a known phenomenon, for example, pro-enzymes. Non-enzymatic reporter systems are also applicable. For example, a green fluorescent protein (GFP) can be used. A permuted GFP, e.g., a GFP with parts rearranged, can serve as the reporter activating protein and the reporter. Action by a protease such as TEV or other protease with the recognition site thereof included in the permuted polypeptide cleaves the permuted reporter activating protein/reporter thereby allowing rearrangement that produces a signal. GFP carries the advantage of itself being a detectable reporter signaling molecule. Alternatively, cleavage sites can be introduced into reporter molecules that do not significantly perturb the signal. Cleavage resulting from the protein-protein interaction then results in reduced reporter signal. Multiple cleavage sites may be introduced into the reporter construct.

Tertiary protein structure can be used to provide guidance to the skilled artisan where cleavage sites are best placed. For example, where two portions of the polypeptide have strong contact, separating these portions by perturbing the sequence would be expected to reduce or eliminate activity. Upon cleavage, the portions would be expected to interact, thus restoring activity.

The first protein of interest may be a membrane-bound protein, such as a transmembrane receptor, e.g., a GPCR. Examples of transmembrane receptors include β-adrenergic receptor (ADRB2), arginine vasopressin receptor 2 (AVPR2 or V2). serotonin receptor 1a (HTR1 A), m2 muscarinic acetylcholine receptor (CHRM2), chemokine (C—C motif) receptor 5 (CCR5), dopamine D2 receptor (DRD2), kappa opioid receptor (OPRK), or α1a-adregenic receptor (ADRA1A), etc. Membrane-bound receptors are well known in the art. It is to be understood that in all cases, the invention is not limited to the specific embodiments described as examples of the present invention. For example, molecules such as the insulin growth factor-1 receptor (IGF-1R), which is a tyrosine kinase, and proteins which are not normally membrane bound, like estrogen receptor 1 (ESR1) and estrogen receptor 2 (ESR2) may be employed in the present invention. The protease or portion of a protease associated with protein B may be a tobacco etch virus nuclear inclusion A (TEV) protease. TEV has a seven residue recognition site and therefore is more specific than proteases with smaller, and statistically more common recognition sites. Other proteases are also appropriate for use with the present invention. For example, enterokinase and factor Xa protease each with a five residue recognition sequence, thrombin and PureAct™ or Clean Cut™ each with a six residue recognition sequence, and PreScission™ with a seven residue recognition sequence are also proteases for use in the present invention. The present invention is not limited to use of any specific protease. The protease must, however, cleave at a site that results in the generated or altered signal from the reporter.

The protein which activates the reporter may be any enzyme that can act on a substrate to produce a detectable signal. For example, the enzyme may directly or indirectly increase or decrease fluorescence or chemiluminescense or may cause a color change. The reporter substrate may be a biologic, such as a protein, or may be a chemical whose reaction is catalyzed by the reporter enzyme. The second protein of interest may be an inhibitory protein, such as an arrestin. Arrestins commonly interact with GPCRs to modulate activity in response to ligand/receptor interaction. The cell may be a eukaryote or a prokaryote. The reporter may be an exogenous component, such as a β galactosidase or a luciferase. For simplicity, "reporter enzyme," is used as an equivalent of a reporter activating molecule, reporter activator, reporter modulating molecule, reporter modulating protein or reporter activating protein, and as shorthand for a molecule that effects a change in reporter output. For example, the reporter enzyme may enzymatically cause a change in the reporter signal or, for example, might enzymatically or non-enzymatically cause a change in signal, such as, a fluorescence signal. The skilled artisan understands various reporter systems and proteins that modulate or activate the reporter signal.

The nucleotide sequence encoding the first protein may be modified to increase interaction with the second protein. Such modifications include, but are not limited to, replacing all or part of the nucleotide sequence of the C terminal region of the first protein with a nucleotide sequence that encodes an amino acid sequence that has higher affinity for the second protein than the original sequence. For example, the C terminal region may be replaced by a nucleotide sequence encoding the C terminal region of AVPR2, AGTRLI, F2RL1, CXCR2/IL-8b or CCR4. Such modifications are known in the art and are an optional feature of the present invention.

Methods of the present invention may comprise contacting a plurality of test compounds with a plurality of samples of cells or units. Each sample may be contacted by one or more test compounds. In another embodiment, a cell or unit carries two different molecules with extracellular domains carrying different reporter activating molecules, both of which interact with β arrestin. Screening is accomplished by determining activity of reporter, e.g., monitoring enzymatic activity in the samples to determine whether any compounds or mixtures of compounds modulate the specific protein/protein interaction. The method may comprise contacting each test sample with a single test compound, may comprise contacting each test sample with a mixture of test compounds, or may combine these features. Compounds that inhibit binding of compounds to protein A may be tested or screened using the present invention. For example, a known ligand of protein A may be included in an assay and compounds that modulate binding of the ligand to the protein can be identified and/or characterized, as in a competition-type assay. Control samples may be present in each assay or may be run in parallel assays.

In some embodiments, the present invention provides a method to determine if a test compound modulates one or more of a plurality of protein interactions of interest. These embodiments, in general, feature: contacting a test compound with a plurality of samples of cells that have been transformed or transfected with: (a) a first nucleic acid molecule including, (i) a polynucleotide which encodes a first protein, and a polynucleotide sequence encoding a cleavage site for a protease, and (ii) a polynucleotide that encodes a protein which activates a reporter in the cell; and (b) a second nucleic acid molecule including, (i) a polynucleotide which encodes a second protein whose interaction with the first protein in the presence of the test compound of interest is to be measured, and (ii) a polynucleotide which encodes a protease or a polypeptide specific for cleaving a polypeptide at the cleavage site. The first protein can differ from other first proteins in a plurality of samples. Then the method comprises determining activity of the reporter in one or more of the plurality of samples as a determination of modulation of one or more protein interactions of interest.

The second protein may be different in each sample or the same in each sample. All samples may be combined in a common receptacle, and each sample may comprise a different pair of first and second proteins. Alternatively, each sample may be tested in a different receptacle. The reporter in a given sample may differ from the reporter in other samples. The mixture of test compounds may comprise or be present in a biological sample, such as cerebrospinal fluid, urine, blood, serum, pus, ascites, synovial fluid, a tissue extract, plant or herbal extract, or an exudate.

In other embodiments, the present invention provides a recombinant cell, transformed or transfected with (a) a nucleic acid molecule including, (i) a polynucleotide which encodes a first protein, (ii) a polynucleotide encoding a cleavage site for a protease, a portion of a protease or a polypeptide with protease activity, and (iii) a polynucleotide which encodes a protein which activates a reporter in the cell, and (b) a nucleic acid molecule which comprises, (i) a polynucleotide which encodes a second protein whose interaction with the first protein in the presence of the test compound is to be measured, and (ii) a polynucleotide which encodes a protease, a portion of a protease or a polypeptide with protease activity which is specific for said cleavage site.

One or both of the nucleic acid molecules may be stably incorporated into the genome of a host test cell. The cell also may have been transformed or transfected with a reporter. The first protein may be a membrane-bound protein, such as a transmembrane receptor, for example, a GPCR. Exemplary transmembrane receptors include ADRB2, AVPR2, HTR1A, CHRM2, CCR5, DRD2, OPRK, or ADRA1A.

The protease or portion of a protease may be, as noted above, is not limited to a tobacco etch virus nuclear inclusion A protease but can be any protein that activates the reporter activating protein, and may be any enzyme that acts upon a substrate to produce a usable or detectable signal. The second protein may be an inhibitory protein. The cell may be a eukaryote or a prokaryote, generally for screening for pharmaceuticals, a eukaryotic cell will be preferred. Cells that glycosylate in a manner similar to the eventual target of a pharmaceutical may be especially preferred. A cell may be cultured or engineered to provide desired glycosylation characteristics. Use of prokaryotic cells that do not match the glycosylation properties of the eventual proposed target may be useful for screening and characterization.

The reporter may be exogenous, for example, a β galactosidase, a GFP or a luciferase. The nucleotide sequence encoding the first protein may be modified to increase interaction with the second protein, e.g., by replacing all or part of the nucleotide sequence of the C terminal region of said first protein with a nucleotide sequence that encodes an amino acid sequence that has higher affinity for the second protein than the original sequence. The C terminal region may be replaced by a nucleotide sequence encoding the C terminal region of, for example, AVPR2, AGTRLI, F2RL1, CXCR2/IL-8B, CCR4, or GRPR.

The present invention comprises as an embodiment, provision of an isolated nucleic acid molecule including, (i) a polynucleotide which encodes a protein (ii) a polynucleotide encoding a cleavage site for a protease, a portion of a protease or a polypeptide with a protease activity, and (iii) a polynucleotide which encodes a protein which activates a reporter in a cell or other assay system. The protein may be a membrane-bound protein, such as is a transmembrane receptor, for example, a GPCR. Exemplary transmembrane receptors include ADRB2, AVPR2, HTR1A, CHRM2, CCR5, DRD2, OPRK, or ADRA1A. The protease or portion of a protease may be a tobacco etch virus nuclear inclusion A protease. As noted above, the protein that activates the reporter may be any protein that interacts with a substrate to produce a signal and need not be limited to the TEV example discussed herein. This or another example of the invention is not to be viewed as limiting the invention to specific embodiments.

In some embodiments, the invention features an expression vector comprising an isolated nucleic acid molecule which comprises, (i) a polynucleotide which encodes a protein (ii) a polynucleotide encoding a cleavage site for a protease, a portion of a protease or a polypeptide encoding a protease activity, and (iii) a polynucleotide which encodes a protein which activates a reporter in the cell, and further being operably linked to a promoter.

In some embodiments, the invention features an isolated nucleic acid molecule that comprises, (i) a polynucleotide encoding a protein whose interaction with another protein in the presence of a test compound is to be measured, and (ii) a polynucleotide which encodes a protease, a portion of a protease or a polypeptide with a protease activity which is specific for the cleavage site. The protein or the other protein may be an inhibitory protein, such as an arrestin.

The invention in some embodiments also features an expression vector comprising an isolated nucleic acid molecule which comprises, (i) a polynucleotide which encodes a protein whose interaction with another protein in the presence of a test compound is to be measured, and (ii) a polynucleotide which encodes a protease or a portion of a protease which is specific for the cleavage site, said nucleic acid further being operably linked to a promoter.

An additional embodiment features a fusion protein produced by expression of: an isolated nucleic acid molecule that includes, (i) a polynucleotide which encodes a protein (ii) a polynucleotide encoding a cleavage site for a protease, a portion of a protease or a polypeptide with protease activity, and (iii) a polynucleotide which encodes a protein which activates a reporter in the cell, and further being operably linked to a promoter; or an isolated nucleic acid molecule that includes, (i) a polynucleotide which encodes a protein whose interaction with another protein in the presence of a test compound is to be measured, and (ii) a polynucleotide which encodes a protease or a portion of a protease specific for the cleavage site.

In yet other embodiments, the invention features a test kit useful for determining if a test compound modulates a specific protein/protein interaction of interest. The test kit comprises one or more of the following: a separate portion of each of (a) a nucleic acid molecule which comprises, a polynucleotide which encodes the first protein (i) a polynucleotide encoding a cleavage site for a protease, a portion of a protease or a polypeptide with protease activity, (ii) a polynucleotide which encodes a protein which activates a reporter gene in the cell, and (b) a nucleic acid molecule which comprises, (i) a polynucleotide which encodes a second protein whose interaction with said first protein in the presence of a test compound is to be measured, (ii) a polynucleotide which encodes a protease or a portion of a protease which is specific for the cleavage site, and optionally containing means for holding each of (a) and (b) separately from each other. The kit may include instructions for use. Alternatively, the kit may contain cells engineered to express either or both of the fused proteins of interest.

The first protein may be a membrane-bound protein, such as a transmembrane receptor. A particular type of transmembrane receptor is a GPCR. A particular transmembrane protein is a GPCR. Exemplary transmembrane receptors include ADRB2, AVPR2, HTR1A, CHRM2, CCR5, DRD2, OPRK, or ADRA1A. The protease, portion of a protease or polypeptide with protease activity may be tobacco etch virus nuclear inclusion A protease. The protein which activates said reporter may be any, for example, protease, which acts on a detectable reporter activating molecule responsive to activation by cleavage. The reporter can be any molecule which yields a detectable signal by the cleavage product. The second protein may be an inhibitory protein, such as an arrestin. The kit may further comprise a separate portion of an isolated nucleic acid molecule which encodes a reporter activating gene. The reporter activator may, for example, be a β galactosidase or a luciferase. The nucleotide sequence encoding said first protein may be modified to increase interaction with the second protein, such as by replacing all or part of the nucleotide sequence of the C terminal region of said first protein with a nucleotide sequence which encodes an amino acid sequence which has higher affinity for the second protein than does the original sequence.

The nucleotide sequence of said C terminal region may be replaced by a nucleotide sequence encoding the C terminal region of, for example, AVPR2, AGTRL1, F2RL1, CXCR2/IL-8B, and CCR4.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." Where corresponding components are described by slightly different wordings, these may not mean a distinguishing of various embodiments, but taken together, the various wordings describe the corresponding elements broadly.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE FIGURES

The attached drawings form part of the present specification and are included to further demonstrate certain aspects of the present invention. The invention may be better understood by reference to one or more of these drawings in combination with the detailed description of specific embodiments presented herein.

FIG. 3 also can be read to show a schematic application of the technology for identification of molecules modulating receptor homodimer or heterodimer formation. Proteins 1 and 33 in this diagram are membrane-bound proteins. Proteins 1 and 33 have been engineered to each include either a protease 22 or a reporter 3 activated by the protease 22. A molecule 4 modulating the interaction binds, e.g., protein 1 and/or 33. When 1 and 33 interact, the protease 22 acts on the reporter activator 3 thereby effecting a changed signal. Heterodimerization can be expanded to include traditional homodimerization. For example, 1 and 33 might be two copies of the same receptor, but differing in the association with protease or reporter. As stated elsewhere, the terms reporter and reporter activator can often be used interchangeably to describe different embodiments of the invention.

DETAILED DESCRIPTION OF SEVERAL EXEMPLARY EMBODIMENTS

The assay of the present invention detects protein-protein interactions without requiring prior knowledge of compounds modulating the interaction or cell pathways initiated by the interaction. The assay can detect interactions of membrane proteins, e.g., formation of homodimers or heterodimers. The assay can detect interactions of a membrane protein with a cytoplasmic protein. The assay can detect interactions of two cytoplasmic proteins. The assay can detect translocation of a protein to intracellular space or to an organelle within the cell. The assay can detect interaction of two cells or packages or units. Either of protein A or B may bind a ligand, cofactor or other compound, molecule or substance, which may or may not be essential or indispensable for the protein-protein interaction.

The term, "sequence," has several uses in the genetic engineering, nucleic acid and protein arts, as known to the artisan, and can have different meanings in the context of a sentence, paragraph, concept, idea, passage and so on. For example, a sequence can represent the particular listing of amino acid residues of a polypeptide (primary structure) or nucleotide bases of a polynucleotide. In another context, a sequence can refer to the composite molecule in a generic sense, such as a polypeptide sequence which refers to the entire molecule without requiring knowledge of the primary amino acid structure. A gene sequence can be synonymous with a gene and refers to the polynucleotide per se or in toto. Sequences can refer to individual polypeptides or polynucleotides, or portions thereof. Hence, when the phrase, "sequences are operably linked," is used, that phrase means that individual genes, domains or transcription units can be ligated or joined in a functional manner to enable expression of the individual gene(s), domain(s), transcription unit(s) and so on resulting from the joining or ligation. The sequences also can be portions of a particular expressed gene or protein, such as the domain(s) of a protein that has a plurality of functional portions or domains. As known in the art, the polynucleotides of interest can be either DNA or RNA, or mixtures thereof, and methods for making and using of same in the practice of the instant invention are known in the art.

Figure 4:
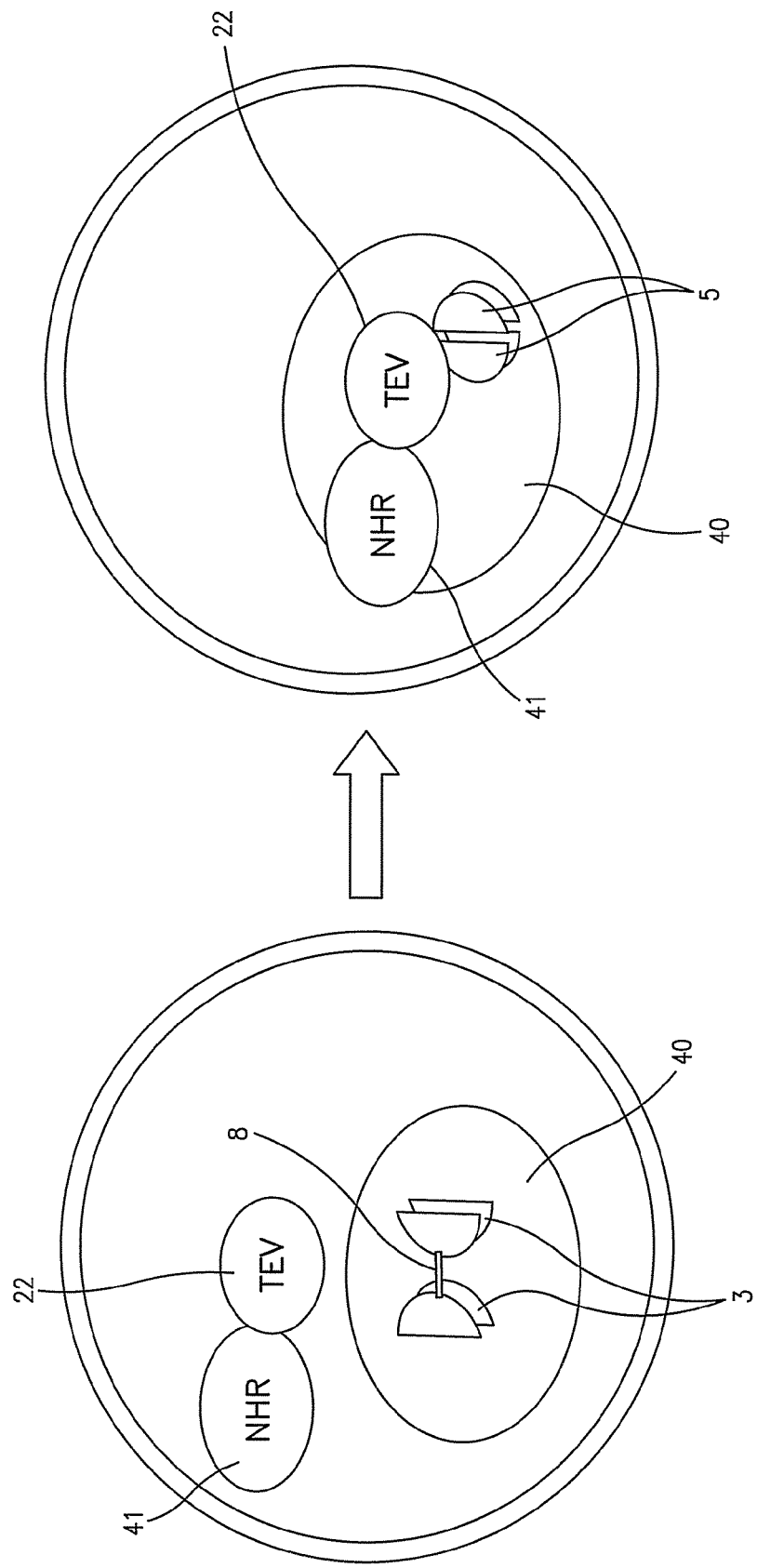
FIG. 4 shows an example involving protein-protein interaction of intracellular proteins. Protein 41 is, e.g., a nuclear hormone receptor, fused to an activator 22, e.g., TEV. A permuted reporter activating molecule 43 is localized in the cell nucleus 40. The reporter can be localized in the nucleus using a basic polypeptide functioning as a nuclear localization peptide sequence. On binding ligand, e.g., a hormone (not shown), the NHR fusion 41 translocates to the nucleus where it interacts with the reporter system.

For example, FIG. 4 shows an assay for modulated activity of a nuclear hormone receptor. Transport of the nuclear hormone receptor to the nucleus causes or instigates a signal by rearrangement of a reporter activating protein and, optionally, a molecule that is detectable and thus can serve as a reporter, such as, fluorescence changes or presence in response to activity of an activating protein, e.g., luciferase. The resulting signal can be any detectable change, e.g., a change in intensity or a change in excitation/emission parameters. Chemiluminescense is another common reporter signal. The skilled artisan will appreciate that either a protease or a permuted reporter can be engineered to have a nuclear or other targeting polypeptide. Such a targeting polypeptide can comprise basic amino acids. Signal would be modulated upon interaction of both in the targeted region.

For GPCRs, the present assay is specific, sensitive, and requires no prior knowledge of the particular G protein for coupling. The assay is not influenced by endogenous GPCRs and can be applied for identifying molecules, including agonists, antagonists, and inverse agonists (for some receptors). The assay of the present invention is an improvement over the assay of Lee et al., avoiding the need for transcription amplification. The present invention provides a more immediate and direct readout.

The present invention provides a simpler and more robust assay system than that of Lee et al., in part because the present system does not require translocation of a reagent to the nucleus and then transcription to amplify the signal. The readout can therefore be proximal to the receptor modulation event. The present invention does not require a nucleus as does the assay of Lee et al. In fact, one application of the present invention is detection of secreted proteins. Either the reporter or protease in the cytoplasm can activate (or inactivate) signal from a secreted partner protein. Another embodiment is use in enucleated cells or in artificial cells, packages or units.

The present invention is especially useful for identifying molecules modulating any protein-protein interaction. The DiscoveRX™ assay, an assay using β arrestin, requires two interacting protein components to remain together at all times for signal generation. Most prior GPCR assays are based on G protein signaling, such as the FLIPR and cAMP assays. Any molecules affecting $Ca^{++}$ or cAMP levels are prone to generate false positive signals. On the other hand, the instant assay is rapid, robust and inexpensive, while being independent of enzyme component association or G proteins signaling, which can impact sensitivity and specificity.

The present invention provides a means to assay or screen any protein-protein interaction by fusing protein A (or protein B) with a reporter activating protein (a reporter modulating protein/molecule or reporter activating protein/molecule is equivalent thereto). An example of such is a permuted enzyme containing a proteolytic cleavage site. Protein B is fused with a protease. Interaction of protein A and protein B can be constitutive or induced by a third molecule. The skilled artisan can use the assay of the present invention to identify molecules that augment or perturb protein interactions. Alternatively, protein A can be fused with a protease and protein B can be fused with a reporter activating protein.

A reporter activating protein of the invention is one which is latent and activatable on interaction with the protease of the second protein. An approach of interest is to produce a reporter activating protein which is a permuted molecule constructed to contain a protease cleavage site. On cleavage, the portions of the reporter activating protein can associate, assemble and so on to produce an active reporter activating polypeptide or assembly. That active, for example, enzymatically active, reporter activating protein then can act on a suitable substrate, for example, a reporter, to yield a detectable signal. Hence, for example, when the permuted, inactive molecule is luciferase, when cleaved to form a biologically active luciferase, that luciferase can act on a suitable substrate, such as a luciferin, to produce a detectable signal, in that case, luminescence.

In another embodiment, the reporter activating protein is a reporter. Hence, that can be viewed as self activation by the reporter activating protein on cleavage. An example would be a GFP, which when cleaved, rearranges and generates a detectable signal independent of a reporter system, such as a reagent that provides a luciferin when the reporter activator is a luciferase.

Permuted reporter activating genes can be constructed in either an active or inactive form. For example, in developing this technology, a GPCR-inactive permuted luciferase fusion was constructed in which the luciferase amino acid sequence order was changed. The original N terminal fragment was moved to the C terminus and the original C terminal fragment was moved to the N terminus and a protease recognition site was used to fuse the two order-changed fragments. Interaction of a GPCR-inactive permuted luciferase fusion protein with β arrestin 2-TEV protease fusion protein results in cleavage of the inactive permuted luciferase and generation of a reconstituted luciferase activity. Using an alternative strategy, the present inventors constructed a GPCR-active permuted luciferase fusion construct in which a protease recognition site is introduced into the original order of luciferase sequence without significant effect on luciferase activity. Interaction of a GPCR-active permuted luciferase fusion protein with a β arrestin 2-TEV protease fusion protein results in cleavage of the active permuted luciferase and produces two inactive luciferase fragments resulting in loss of activity, and hence diminution or loss of signal.

The reporter activating protein can be selected from permuted protein based reporters such as Gaussia luciferase; renilla luciferase; β lactamase; β galactosidase; and fluorescent proteins, such as one of the green fluorescent proteins (GFP) or DsRed proteins, etc. containing, for example, a proteolytic cleavage site, such as, a TEV cleavage site. Although "enzyme" is used as a general term, the reporter activating protein is not per se limited to "enzymes" but to any reporter activating protein that can effect a change in a signal. For example, binding or sequestering a fluorescent protein may be a sufficient signal change without a chemical reaction changing molecular structure.

As one feature of the present invention, permuted luciferase variants can be constructed using different breaking points and with different overlapping regions to reduce or increase protease activity, basal luciferase activity or a reconstituted luciferase activity by a skilled molecular biologist or protein chemist. Rachel B. Kapust, et al. *Biochemical & Biophysical Research Communications,* 294 (2002) 949-955.

Proteases are known in the art and can be selected from diverse sources, e.g., bacteria, yeast, fungi, plant, insect, mammal etc. Organisms require proteases to process peptides and therefore the biologic world presents many diverse proteases suitable for use in the present invention. Selection of appropriate cleavage sites for a desired enzyme generally can be found in the literature or in product catalogues. Such protease cleavage sites are oligopeptides of varying length, such as two amino acids, three amino acids, four, five, six, seven, eight, nine, ten or more amino acids, and so on.

The permuted reporter activating protein can also be replaced with alternate protease cleavage sites or linked to one or more inactive pre-pro-enzymes that can be converted to active enzymes after cleavage. For example, cleavage sites of pre-pro-enzymes can be modified to be sensitive to an enzyme that recognizes a sequence that differs from the wild type. Alternatively, the cleavage site can be modified for a particular desired effect, such as greater specificity, greater susceptibility to cleavage and so on.

The assay can also be accomplished using an active enzyme with a protease cleavage site that is converted to an inactive enzyme after the cleavage. This feature provides some simplicity as multiple proteolytic enzymes with different specificities can then act on the active enzyme as desired with no or only minimal re-engineering.

Mammalian cells, such as HEK293, COS-7, NIH3T3, etc. as well as yeast cells can be used to establish the protein-protein interaction permuted reporter activating protein assay. Cell-free systems can also be used. Such cell-free systems include lysates, membrane preparation, virus stock, virus-like particles, liposomes, platelets, membrane preparations, cochleates, other artificial lipid-based units or packages that simulate biological membranes to form a structure than can enclose, attach, carry, include and so on a biological entity, such as a transmembrane protein. Organisms can be used, such as transgenic organisms, in an assay of interest, or can contribute cells or reagents that can be used in an assay of interest.

The instant assay also provides for a detectable reporter. That reporter is one which is a substrate for the reporter activating protein of interest. Hence, in the case of permuted luciferase, a suitable reporter is a luciferin which when acted on by a luciferase yields a detectable luminescence signal. Reporter can be intracellular to provide an assay that avoids cell lysis. For example, GFP fused to the carboxyl terminus of maltose binding protein (MBP) is not fluorescent when the MBP signal sequence is present. When the MBP signal peptide is removed, fluorescence is observed. Feilmeier et al., J Bacteriol 182 (14) 4068-4076, 2000. Hence, a protease cleavage site can be introduced downstream of the MBP signal peptide as taught herein to yield an assay that can be conducted using live cells.

The assay can be applied to monitor subcellular location and translocation of a protein interaction complex by using permuted luciferase or fluorescent proteins. FIG. 4 shows a schematic of such an embodiment.

The present invention relates to methods for determining if a substance of interest modulates interaction of i) a first protein, such as a membrane-bound protein, e.g., a receptor, such as a transmembrane receptor, with ii) a second protein, such as an intracellular molecule, another transmembrane protein and so on, e.g., member of the arrestin family. One methodology involves cotransforming or cotransfecting a cell, which may be prokaryotic or eukaryotic, with two constructs. The first construct includes, a first nucleic acid encoding (a) the first protein, such as a transmembrane receptor, and (b) a cleavage site for a protease, and (c) a second nucleic acid encoding a protein that activates a reporter. The second construct includes, (a) a nucleic acid which encodes a second protein whose interaction with the first protein is measured and/or determined, and (b) a nucleic acid which encodes a protease, a portion of a protease or a polypeptide with a protease activity that acts on the cleavage site of the first construct. In some embodiments, one or more of these constructs may become stably integrated into the cells.

Figure 1:
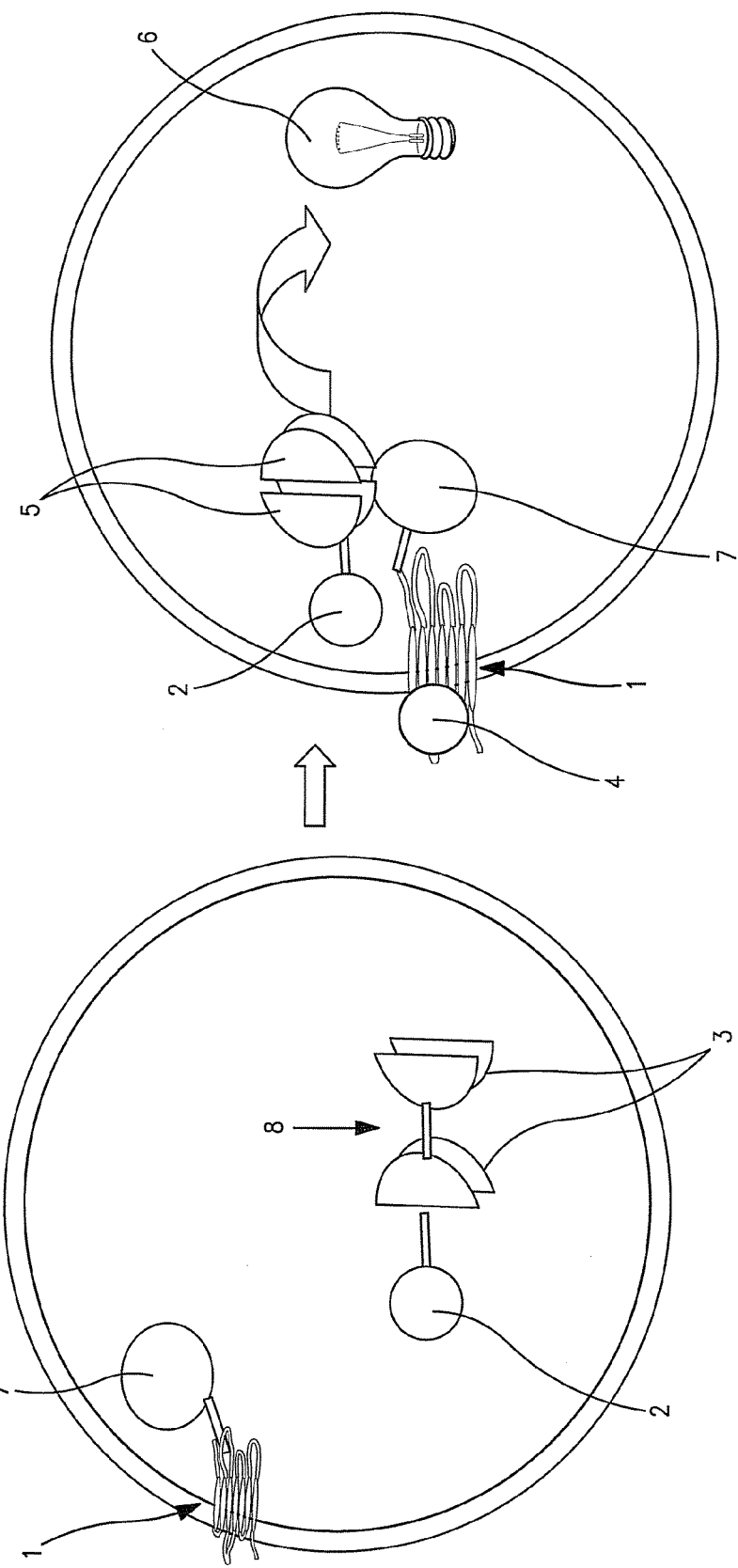
FIG. 1 shows a schematic of one embodiment of the application wherein a modulator 4 binds a protease-associated protein 1 causing the protein to interact with a second protein 2 associated with a reporter modulator 3 such as a permuted inactive modulating protein. The modulator 4 represents a compound modulating protein-protein interaction. In this example, e.g., Ar or arrestin 2, is fused to an inactive permuted reporter modulating or activating protein 3. A protease 7 is associated with a protein 1. A cleavage site 8 is shown between the two segments of the reporter modulating protein 3. When protease cleavage occurs following interaction with the modulator 4, attached to the Protein 1, e.g., a 7TMR, the reporter activating protein activity is reconstituted, ultimately resulting in a detectable signal, represented by the light bulb 6.
Figure 2:
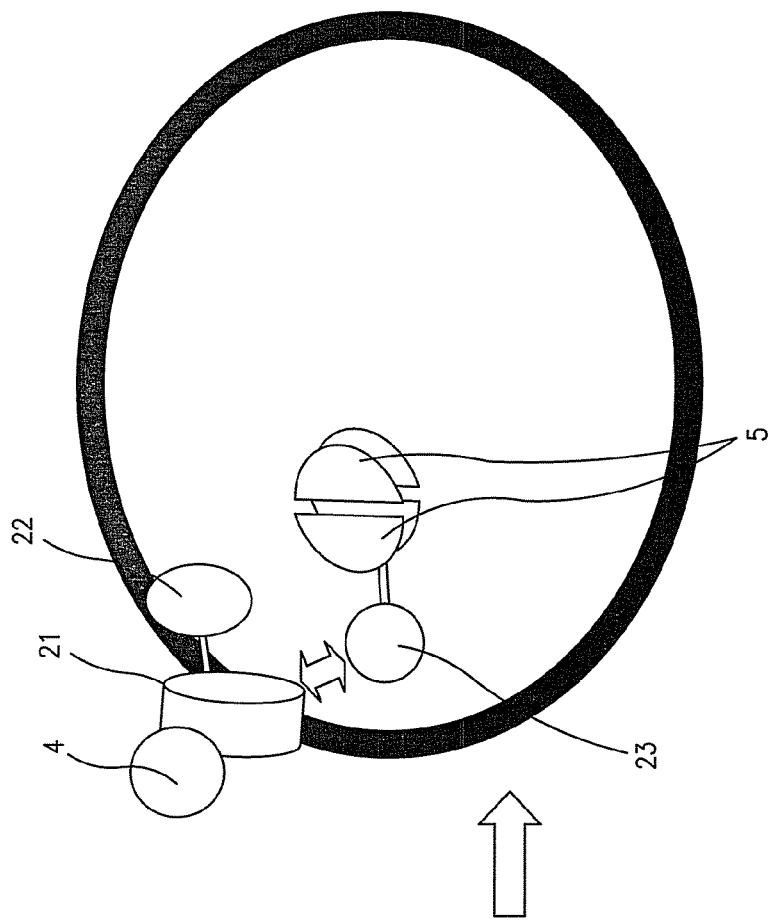
FIG. 2 is a diagrammatic representation of one protein-protein interaction assay of the present invention. A membrane-bound protein 21 with an intracellular protease 22 attached interacts with a modulator 4. An inactivated reporter associated protein 23 carries an inactive reporter 3 or reporter activator 3. Upon interaction, the protease 22 associated with protein 21 cleaves the cleavage site of the permuted reporter activating protein 23 thereby allowing rearrangement 5 of the protein portions of the reporter activating protein 3 when the modulator 4 engages protein 21. The reporter activator thereby effects reconstitution of the reporter or reporter activator 3 to elicit or activate a report.
Figure 2:
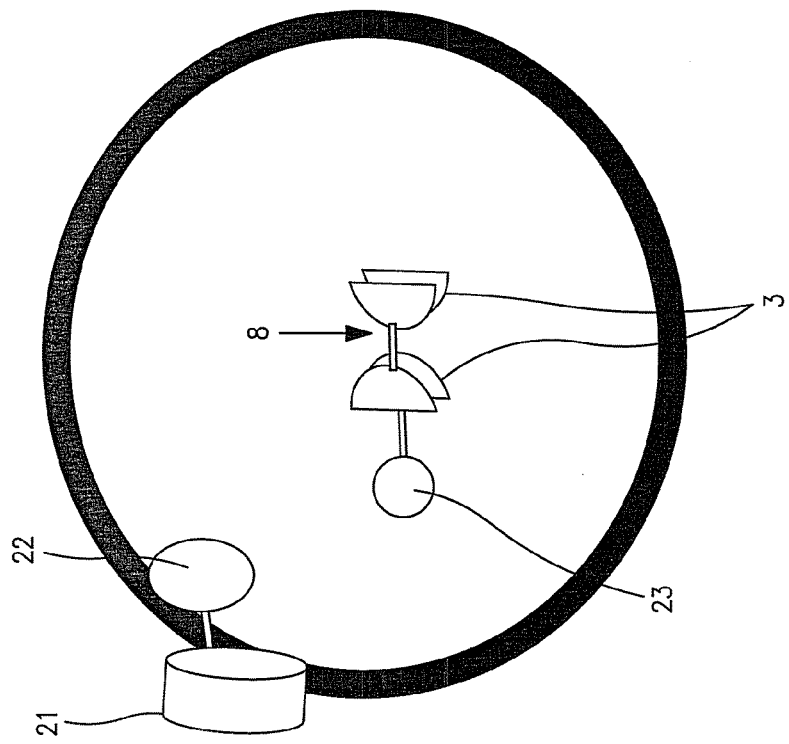
Figure 3:
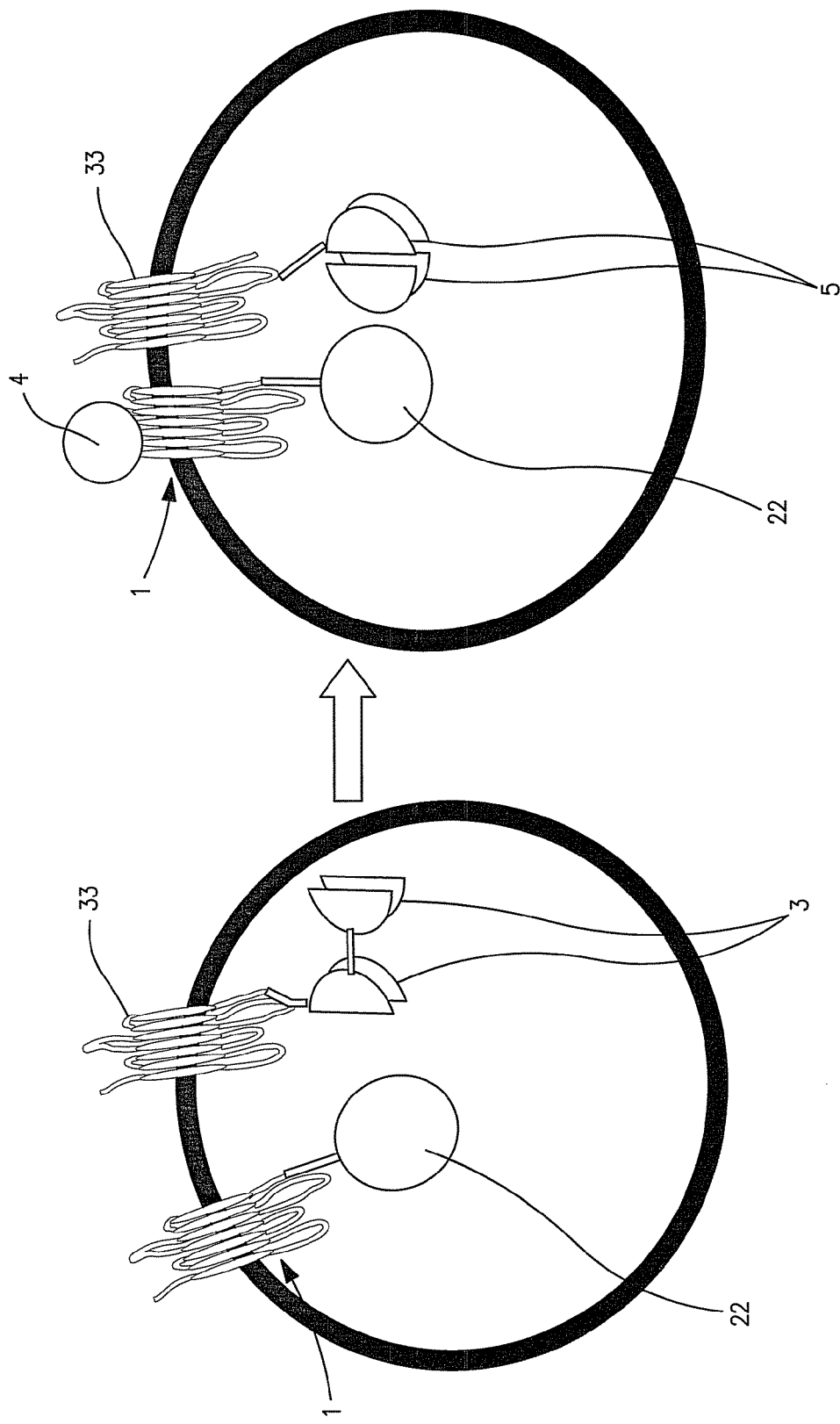
FIG. 3 shows a schematic of an embodiment where two transmembrane proteins interact. A molecule 4 causes (modulates) an interaction between the two membrane proteins, e.g., at least one receptor protein. In this drawing, a protease 22, e.g., (TEV (7 in FIG. 1), is attached to a protein 1 and is brought in proximity with a permuted reporter activator fusion protein 3 attached to a second membrane protein 33. Proteolysis at a cleavage site 8 enabled by the proximity of the proteins 1, 33 results in activation 5 of the reporter activating protein 3.

Features of an embodiment of the invention are shown, pictorially, in FIG. 1. In brief, a cell is obtained that expresses a first protein of interest. The protein of interest may include a proteolytic portion or the proteolytic portion may associate with a complex upon binding or release of a bound ligand. An inactive enzyme is attached to a peptide portion that associates with the first protein of interest in response to a change in ligand binding. Proximity of the protease to the inactive enzyme allows, in this embodiment, reconstitution of activity of the enzyme, e.g., a luciferase. The reconstituted activity affects the report of that protein-protein interaction.

The example shown in FIG. 1 depicts a transmembrane protein, a TEV cleavage enzyme, a permuted luciferase and a substrate for luciferase, e.g., a luciferin. The protein "A" may be an arrestin in this example. The first protein of interest may be a GPCR. The N and C terminals of luciferase can be rearranged and can be linked with a TEV protease cleavage site to generate an inactive, permuted luciferase. The permuted luciferase as shown is fused with β arrestin 2.

Protein A can be fused with a protease. Protein B can be fused with an inactive permuted reporter activating protein. A protease recognition and cleavage site (which is recognized by a protease fused to the protein A) is inserted into the permuted reporter activating protein. Protein A and protein B are brought to proximity, e.g., by a third molecule that modulates protein A and protein B interaction. Proteolysis of permuted inactive reporter activating protein by the fusion protease in proximity results in fusion of the two fragments of permuted reporter activating protein to regenerate active reporter activating protein activity. The activity of reporter activating protein can be assessed by appropriate reagents and apparatus using a suitable reporter, such as, luciferin, using commercially available reagents and kits.

A GPCR as protein A can be fused with a TEV protease. Alternatively, that GPCR can be fused with a permuted reporter activating protein.

In FIG. 1, a molecule that binds to a GPCR causes β arrestin interaction with the GPCR. Proteolysis of the cleavage site within permuted luciferase by TEV protease bound to, or in the proximity of, protein A generates luciferase protein fragments. The fragments reconstitute active luciferase which is detected or the presence of which is inferred using a suitable reporter for luciferase activity, such as a luciferin in the cell or in a lysate.

The method can produce specific signals for receptor proteins such as GPCRs, which may act with a G protein or a β arrestin.

The general method as shown in FIG. 1 is applicable generally to GPCRs since beta arrestin recruitment is a common phenomenon. However, any pair of molecules that interact, bind, associate and so on or are suspected of interacting, binding, associating and so on can be used in the practice of the instant invention.

An exemplified method uses a β arrestin signaling pathway and requires no prior knowledge of specific G protein coupling because the current assay is not specific to the GPCR or to the involved G protein. Hence, this assay is desirable for orphan GPCRs in which the G protein coupling pathway is unknown. The method produces immediate and physiologically relevant readouts without transcriptional amplification as in the assay of U.S. Pat. No. 7,049,076 (Lee et al.).

The materials and methods also enable monitoring G protein independent phenomena. In that case, a β arrestin can be labeled with the permuted reporter activating protein. A molecule suspected or known to interact with β arrestin can be labeled with the suitable protease, such as a GPCR that demonstrates β arrestin bias.

The present invention has advantage over enzyme fragment complementation assays (such as DiscoveRX PathHunter™ β arrestin assay) in which the interaction partners have to remain engaged or together to ensure enzyme fragment complementation. On the other hand, in the present assay, once proteolysis occurs due to proximity of the reagents, the active reporter activator is generated, and protein interaction partners are not required to remain associated to obtain a properly informative assay.

Nucleic acid encoding this first fusion protein and other peptide components can be introduced into a host cell. Such cell engineering is well known in the art. Nucleic acid for the various peptides may be engineered as a single molecule or may be introduced serially or in parallel. Some of the constructs can become integrated into a host chromosome, for example, to obtain stable transfection, practicing materials and methods known in the art.

In an alternative system, the two proteins of interest may interact in the absence of a ligand or test compound. The ligand or test compound may cause the two proteins to dissociate, change conformation, or otherwise lessen or inhibit their interaction. In such a case, the level of free, functionally active proteolytic enzyme in the cell decreases in the presence of a positive test compound, leading to a decrease in proteolysis, and a measurable decrease in the activity of the reporter activating protein.

In an exemplary embodiment, an arrestin is the second protein that binds to the transmembrane receptor in the presence of an agonist; however, it is to be understood that since receptors are but one type of protein, the assay is not dependent on the use of receptor molecules, and agonist binding is not the only interaction capable of being involved. Any protein that interacts with a second protein will suffice, although the interest is in transmembrane proteins because of their role in eliciting cell, organ and tissue reactions on exposure of the receptor to a modulator that precipitates the cell bound receptor into an active state. Further, agonist binding to a receptor is not the only type of binding which can be assayed. Inverse agonists also can be tested in the instant assay. One can determine antagonists, per se, and also determine the relative strengths of different antagonists and/or agonists in accordance with the invention.

Other details of the invention, including specific methods and technology for making and using the subject matter thereof, are described below.

As with the method described herein, the products which are features of the invention can be simply described. For example, in the "three part construct," i.e., a construct having sequences encoding i) a protein, ii) the cleavage site, and iii) the reporter activating protein; the protein may be, for example, an intracellular protein or a membrane-bound protein, such as a transmembrane receptor, e.g., a member of the GPCR family. The cleavage site may be any hydrolysable site whose hydrolysis can be accomplished by action of a protease of a partner protein of the protein-protein interaction. Cleavage may directly produce the report or cleavage may allow rearrangement of a reporter activating protein to effect report from another molecule. The third part can instead be a protease or a polypeptide with protease activity.

These sequences can be modified so that the C terminus of the proteins they encode have better and stronger interactions with the second protein. The modifications can include, e.g., replacing a C terminal encoding sequence of the protein, such as a GPCR, with the C terminal coding region for AVPR2, AGTRLI, F2PLI, CCR4, CXCR2/IL-8 and so on. The gene sequences can be recoded to optimize translation of the proteins of interest in a host cell of interest.

The protein that activates the reporter may be a protein which acts within the cytoplasm or within an organelle, such as the nucleus, or it may be a molecule that sets a cascade of reactions in motion, resulting in action by another protein. The skilled artisan is well versed in such cascades as they are well-studied cellular events. For example, translocation signals, such as a nuclear translocation sequence may be incorporated in the reporter enzyme. Localization sequences are known in the art.

A second construct, as described supra, includes a region which encodes a protein that interacts with the first protein, leading to some measurable phenomenon. The protein may be an activator, a competitor, an inhibitor, one that provides a synergistic response and so on, or, more generically, a "modulator" of the first protein. Members of the arrestin family are exemplified, especially when the first protein is a GPCR, but other protein encoding sequences may be used, especially when the first protein is not a GPCR. The second part of these two part constructs encodes the protease, portion of a protease or a polypeptide with protease activity, which acts to cleave the reporter activating protein encoded by the first construct to yield reporter activating protein capable of yielding, directly or indirectly, a detectable signal.

However, these exemplified embodiments do not limit the invention, as discussed in the following additional embodiments provided herein, for example, the protease can be fused to protein A or protein B as a design choice.

Host Cells

As used herein, the terms "cell," "cell line," and "cell culture" may be used interchangeably. Host cells may also refer to a source cell from which a lysate might be obtained. All of these terms also include their progeny, which is any and all subsequent generations. It is understood that all progeny may not be identical due to deliberate or inadvertent mutations, selection or differentiation. The host cells may have been engineered to express a screenable or selectable marker or reporter which yields a signal when acted on by the reporter activating protein of the first construct that is cleaved by the protease that is part of a fusion protein of the second construct. The screenable marker or reporter may be introduced to the host cell or assay system in any manner.

Numerous cell lines and cultures are available for use as a host cell. For example, many can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537), *E. coli* W3110 (F⁻, lambda⁻, prototrophic, ATCC No. 273325), DH5α, JM109, and KC8), bacilli such as *Bacillus subtilis*; and other enterobacteriaceae such as *Salmonella typhimurium, Serratia marcescens*, various *Pseudomonas* species, as well as a number of commercially available bacterial hosts such as SURE® Competent Cells and SOLOPACK™ Gold Cells (STRATAGENE®, La Jolla). In certain embodiments, bacterial cells such as *E. coli* LE392 may be used as host cells for phage viruses.

Examples of eukaryotic host cells for replication and/or expression of a vector include, but are not limited to, HeLa, NIH3T3, Jurkat, 293 (HEK), COS, CHO, Saos, and PC12. Other cells such as yeast cells or insect cells, e.g., Sf9 cells, are also suitable. It is discretionary upon the skilled artisan to employ the host cell he or she wishes to use for the intended purpose. Many host cells from various cell types and organisms are available and are known to one of skill in the art.

Similarly, a viral vector (including a phage) may be used in conjunction with either a eukaryotic or prokaryotic host cell, particularly one that is permissive for replication or expression of the vector. The host cell is not necessarily an immortalized cell line. The host cell may be from a stem cell culture or a primary cell culture, such as hematopoietic stem cells, vascular, epithelial, smooth muscle, splenic, T cell, B cell, monocyte, etc. The host cell may be transgenic, e.g., comprising genetic material from another organism. Cells incapable of use in the method of Lee et al. are suitable for the assay of the present invention because active transcription is not required. For example, enucleated cells, such as red blood cells or platelets, are capable of use in the present invention.

In the context of the instant assay, the host cell is meant to include artificial packages and units, such as liposomes and virus-like particles, for example. Such structures often mimic or simulate a cell or parts thereof, which yield an enclosure with an internal void separate totally or partially from the exterior by a film, membrane or other structure. As mentioned, such artificial packages and units include liposomes, cochleates, virus-like particles, viruses and so on.

Proteins

The present invention contemplates the use of any two proteins for which a physical interaction is known or suspected. In some embodiments, the proteins will exist or be engineered to exist as fusions proteins, a first protein fused to a latent or inactive reporter activating polypeptide, and the second protein fused to a protease that recognizes a cleavage site in the first fusion protein, cleavage of which releases the reporter activating polypeptide or enables activity of same.

With respect to the first protein of interest, the first protein may be, e.g., a naturally occurring membrane-bound protein, or one which has been engineered to become membrane-bound. For example, the first protein may be a transmembrane receptor such as a GPCR, or any other transmembrane receptor of interest, including, but not being limited to, receptor tyrosine kinases, receptor serine/threonine kinases, cytokine receptors, and so forth. Further, as it is well known that portions of proteins will function in the same manner as the full length first protein, such active portions of a first protein, such as the extracellular domain and the transmembrane domain, are encompassed by the definition of protein herein.

As will be evident to the skilled artisan, the present invention may be used to assay for interaction with any protein, and is not limited in its scope to assaying membrane-bound receptors, such as the GPCRs. For example, the activity of other classes of transmembrane receptors, including, but not limited to: receptor tyrosine kinases (RTKs), such as IGF1R, such as the epidermal growth factor receptor (EGFR), ErbB2/HER2/Neu or related RTKs; receptor serine/threonine kinases, such as Transforming Growth Factor-β (TGFβ), activin, or Bone Morphogenetic Protein (BMP) receptors; cytokine receptors, such as receptors for the interferon family for interleukin, erythropoietin, G-CSF, GM-CSF or tumor necrosis factor (TNF); leptin receptors; and other receptors, which are not necessarily normally membrane-bound, such as estrogen receptor 1 (ESR1), and estrogen receptor 2 (ESR2). In each case, the method may involve transfecting a cell with a modified receptor polynucleotide that directs the expression of a chimeric or fusion protein including the receptor of interest, a protease cleavage site and a reporter activating polypeptide. The cell may be cotransfected with a second polynucleotide, e.g., a vector that directs the expression of a chimeric or fusion protein including an interacting protein fused to the protease that recognizes and cleaves the cleavage site of the first protein. The first and second polynucleotides may be included in a single molecule, thus avoiding cotransfection. In the case of RTKs, such as the EGFR, this interacting protein may consist of an SH2 (Src homology domain 2) containing polypeptide, such as phospholipase C (PLC) or a Src homology 2 domain containing transforming protein 1 (SHC1). In the case of receptor serine/threonine kinases, such as TGFβ, activin and BMP receptors, this interacting polypeptide may be a Smad protein or portion thereof. In the case of cytokine receptors, such as interferon α, interferon β or interferon γ receptors, this interacting protein may be a signal transducer and activator of transcription (STAT) protein such as, but not limited to, Stat1 or Stat2; or Janus kinase (JAK) proteins, Jak1, Jak2 or Tyk2; or portions thereof, and so on. The transfected cell can contain a reporter acted on by a reporter activating protein. An assay is then performed in which the transfected cells are treated with a test compound for a specific period and the reporter activity is measured at the end of the test period. If the test compound activates the receptor of interest, interactions between the receptor of interest and the interacting protein are stimulated, leading to cleavage of the protease site and activation of the reporter activating protein, which is in turn, results in a measurable change or increase in reporter activity.

Other possible protein pairs include antibody-antigen, enzyme-substrate, dimerizing proteins, components of signal transduction cascades, component(s) of a composite structure, such as a ribosome or a virus, intercellular interacting molecules on different cells, such as an antigen presenting cell and an immune cell for response, such as a T cell, a B cell, an NK cell, a dendritic cell, a monocyte, a macrophage and so on, and other protein pairs known to the art. The protease and protein having a protease recognition site are interchangeable with respect to which protein, e.g., A or B, to which each is attached or associated.

Reporters

Reporters may be any molecule that changes appearance or function in response to activity of an active reporter activating molecule and yields a detectable signal or can be readily monitored to track those changes. These terms are meant to be applied loosely. The reporter activating protein once activated (or in some possible embodiments, inactivated), causes a detectable change in the reporter. Detecting this change is used to determine whether e.g., a test compound has modulated a protein-protein interaction. Other non-enzyme reporter activating proteins can be used so long as a detectable signal is produced. Hence, known reporter activating proteins can be used, such as galactosidases, peroxidases, luciferases and so on. Known reporters can be used, such as galactosidase substrates, peroxidases substrates, luciferase substrates, GFP's and so on.

Proteases and Cleavage Sites

Proteases are well characterized enzymes that cleave other proteins at a particular site. One family, the Ser/Thr protease family, cleaves at serine and/or threonine residues. Other proteases include cysteine or thiol proteases, aspartic proteases, metalloproteinases, aminopeptidases, di & tripeptidases, carboxypeptidases, and peptidyl peptidases. The choice of these is left to the skilled artisan and need not be limited to the molecules described herein. It is well known that enzymes have catalytic domains and these domains can be used in place of full length proteases. Such are encompassed by the invention as well. A specific embodiment is the tobacco etch virus nuclear inclusion A protease (TEV), or an active portion thereof. Other specific cleavage sites for proteases may also be used, as is understood by the skilled artisan.

Modification of Proteins

The first protein may be modified to enhance its binding to the interacting protein in some embodiments of this assay. For example, it is known that certain GPCRs bind arrestins more stably or with greater affinity upon ligand stimulation and this enhanced interaction is mediated by discrete domains, e.g., clusters of serine and threonine residues in the C terminal tail (Oakley, et al, *J. Biol. Chem.*, 274:32248-32257, 1999 and Oakley, et al., *J. Biol. Chem.*, 276:19452-19460, 2001). Using this as an example, it is clear that the receptor encoding sequence itself may be modified, so as to increase the affinity of the membrane bound protein, such as the receptor, with the protein to which it binds. Exemplary of such changes are modifications of the C terminal region of the membrane bound protein, e.g., a 7TMR, which may involve replacing a portion of it with a corresponding region of another receptor that has higher affinity for the binding protein, but does not impact receptor binding function.

In addition or alternatively, the second protein may be modified to enhance its interaction with the first protein. For example, the assay may incorporate point mutations, truncations or other variants of the second protein, e.g., arrestins, that are known to bind agonist-occupied GPCRs more stably or in a phosphorylation-independent manner (Kovoor, et al., *J. Biol. Chem.*, 274:6831-6834, 1999). Such changes can be made practicing methods known in the art.

Assay Formats

The present invention, in several embodiments, offers a straightforward way to assess the interaction of two proteins when expressed in the same cell, unit or reaction mixture. A first construct may comprise a sequence encoding a first polypeptide, concatenated to a polynucleotide encoding a cleavage site for a protease, a protease portion or a polypeptide with a protease activity, which is itself concatenated to a polynucleotide encoding a reporter enzyme. "Concatenated" describes a situation where the sequences described are fused to produce a single, intact open reading frame, which may be translated into a single polypeptide which contains all the elements. These may, but need not be, separated by additional nucleotides which may or may not encode additional proteins or peptides. A second construct inserted into the recombinant cells may contain both a polynucleotide encoding a second protein and the protease, protease portion or polypeptide encoding a protease activity. Together, these elements form a basic assay format when combined with a candidate agent whose effect on target protein interaction is sought.

However, the invention may also be used to assay more than one membrane-bound protein, such as a receptor, simultaneously by employing different reporters, each of which is stimulated by the activation of a protein, such as the classes of proteins described herein. For example, this may be accomplished by mixing cells transfected with different receptor constructs and different reporter activating proteins, or by fusing different enzymes for each test receptor, and measuring the activity of each reporter gene upon treatment with the test compound(s). For example, it may be desirable to determine if a molecule of interest activates a first receptor and also to determine if side effects should be expected as a result of interaction with a second receptor. In such a case one may, e.g., involve a first cell line encoding a first receptor and a first reporter activating protein, such as lacZ, and a second cell line encoding a second receptor activating protein and a second reporter, such as GFP. In that circumstance, a GFP can be permuted as practiced in the instant invention. One would mix the two cell lines, add the compound of interest, and look for a positive effect on one, with no effect on the other.

The invention in alternate formats relates both to assays where a single pair of interacting proteins is examined, but also to what will be referred to herein as "multiplex" assays. Such assays may be carried out in various ways, but in all cases, more than one pair of proteins is tested simultaneously. This may be accomplished, e.g., by providing more than one sample of cells, each of which has been transformed or transfected, to test each interacting pair of proteins. The different transformed cells may be combined, and tested simultaneously, in one receptacle, or each different type of transformant may be placed in a different well, and then tested. Alternatively, a cell can be manipulated to carry plural labeled first proteins, such as, transmembrane-based proteins, to determine whether a ligand or a candidate molecule activates more than one receptor.

The cells used for the multiplex assays described herein may be, but need not be, the same. Similarly, the reporter system used may be, but need not be, the same in each sample. After the sample or samples are placed in receptacles, such as wells of a microarray, one or more compounds may be screened against possibly the plurality of interacting protein pairs set out in the receptacles.

Figure 10:
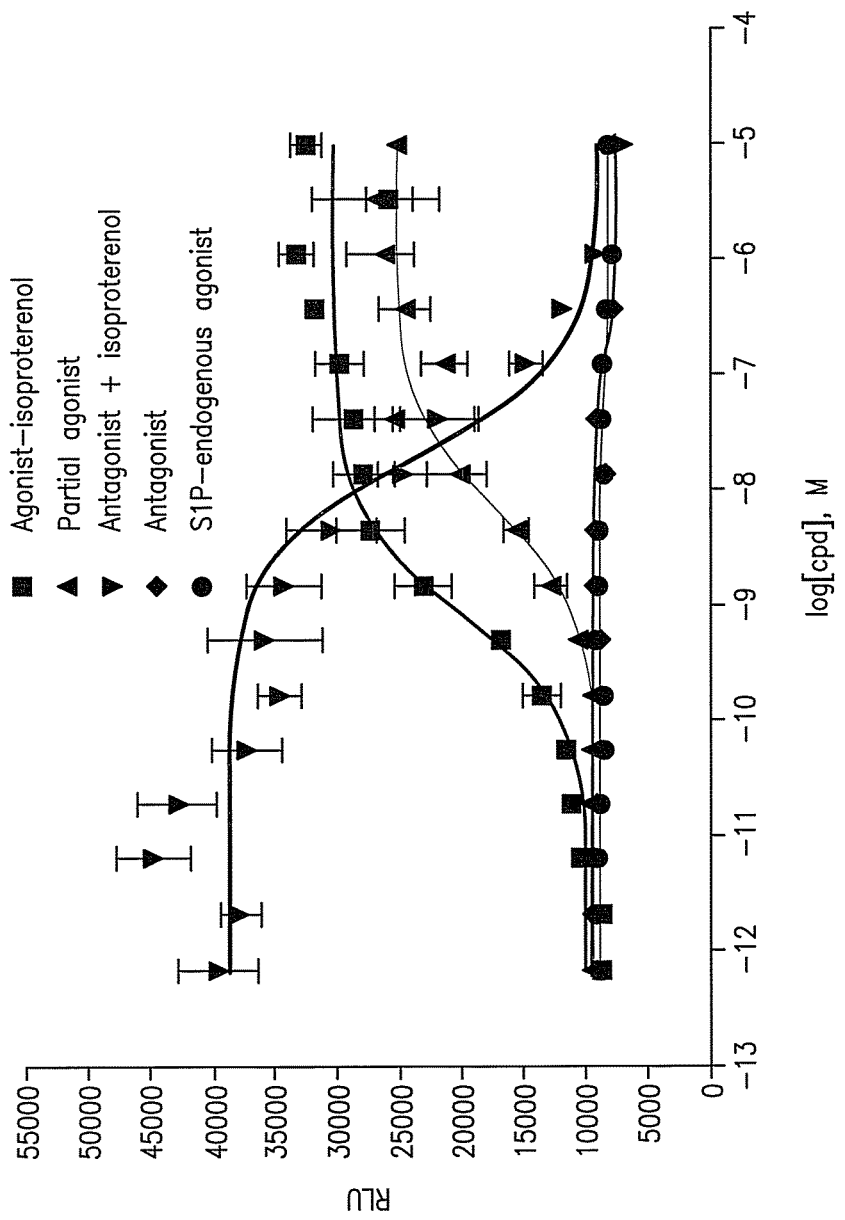
FIG. 10 shows an evaluation of a Per-Luc assay for agonist (isoproterenol) (■), partial agonist (▲) antagonist plus isoproterenol (▼), antagonist (♦) and a non-specific endogenous receptor (●) responses in HEK cells stably expressing an arrestin/permuted enzyme construct and transiently transfected with ADRB2-TEV.

FIG. 10 is indicative of common results obtained using the present assay. At low or high concentrations (depending on whether the modulation is inhibitory or activating) a test compound may have no effect. As concentration of the test compound decreases or increases, the modulatory effect can change. A dose response curve such as shown in FIG. 10 may be used to assess modulation. A single point can also be evaluated. For example, the point might be a predetermined value different from the control or background, often determined on a statistical basis by accumulating data or running multiple samples of "normal' subjects to obtain a sample population mean value with standard errors and deviations. A constant may be used as a predetermined difference value. Generally one uses ratios, e.g., at least 10% from control, but more often a multiple of control, e.g., about 1.5, 2, 2.5, 3, 4, 5, 10, 20, 50, 100, 200, 500, 1000 or more (or reciprocals thereof) times a control value which may be predetermined in another assay run. The predetermined threshold to signify modulation is routinely calculated by the skilled artisan taking into account balancing type 1 and type 2 errors as the situation suggests or requires.

Kits

Any of the compositions described herein and combinations thereof may be provided in a kit. The kits will thus comprise, in suitable container(s), one or more of the components, e.g., the vectors or cells of the present invention, and any additional agents that can be used in accordance with the present invention.

The kits may comprise one or more suitably aliquoted compositions of the present invention. The components of the kits may be packaged either in aqueous medium or in lyophilized form or as a concentrate in a suitable solvent for the solute. The container(s) of the kits generally will include at least one vial, test tube, flask, bottle, syringe or other container, into which a component may be placed or has been placed, and preferably, suitably aliquotted. Where there are more than one component in the kit, the kit also will generally contain a second, third or other additional container into which the additional components may be separately placed. However, various combinations of components may be comprised in a single container, such as a vial. Also, suitable diluents may be provided. The kits of the present invention also will typically include a means for containing reagent containers in close confinement for commercial sale. Such containers may include injection or blow-molded plastic or foam containers into which the desired vials are retained, along with printed instructions.

When components of a kit are provided in one and/or more liquid solutions, the liquid solution may be an aqueous solution, such as a sterile aqueous solution being particularly useful. However, the components of the kit may be provided as dried powder(s) or on a solid support. When reagents and/or components are provided as a dry powder, the powder can be reconstituted by the addition of a suitable solvent. It is envisioned that the solvent, such as sterile water or a suitable saline or buffer may also be provided in another container.

EXAMPLES

Specific embodiments describing the invention will be seen in the examples which follow, but the invention should not be deemed as limited thereto.

Example 1

FIG. 1 shows an embodiment that includes a permuted, inactive luciferase whose activity is reconstituted by action of TEV protease on a TEV protease recognition site contained therein. The first protein, as shown, is fused with a protease. Example 1 was designed to use TEV protease activity to reconstitute activity of permuted luciferase as an embodiment of the second protein. The second protein, as shown, is fused with an inactive permuted reporter activating protein, luciferase. A protease recognition and cleavage site which is recognized by a protease fused to the protein of interest was inserted into the permuted reporter activating protein. The first protein and the second protein are brought to proximity by a third molecule that modulates the interaction between the first protein and the second protein. Proteolysis of permuted, inactive reporter activating protein by the fusion protease in proximity results in the cleavage forming the two fragments of permuted reporter activating protein to regenerate active reporter activating protein. The activity of reporter activating protein can be assessed by appropriate reagents and apparatus.

Permuted luciferase was constructed by rearranging firefly luciferase N terminal amino acids 2 to 233 and C terminal amino acids 234 to 550 in reverse order, interrupted by a TEV protease recognition site, ENLYFQX (SEQ ID NO:3). Cleavage at this site results in reconstituted activity of the permuted luciferase. The position X can be any amino acid that dictates TEV protease recognition affinity and cleavage efficiency.

Varying X has been shown to modulate the enzyme kinetics of TEV. Similar amino acid substitutions at other sites of the recognition sequence also can alter kinetics. Modulating kinetics is advantageous to optimize, for example, incubation times in the screening process and background activity that affects signal/noise parameters. The permuted luciferase (luc234X233, where X is the particular amino acid at the N terminus of the TEV heptapeptide cleavage site, SEQ ID NO:3) was then fused to the C terminus of a GPCR, ADRB2, to generate the GPCR-permuted luciferase, ADRB2-luc234X233, expression plasmid.

Example 2

Human β arrestin 2-TEV fusion plasmid was constructed by fusing tobacco etch virus protease A to the C terminus of β arrestin 2. All DNA fragments were generated by PCR using appropriate templates. GPCR-luc234X233 fusion genes were subcloned in pcDNA3.1(+) with a neomycin selection marker (Invitrogen) and Arr-TEV fusion genes were subcloned in pcDNA3.1(+) with a zeocin selection marker (Invitrogen Cat. #43-0018).

Example 3

CHO-K1 cells were co-transfected with ADRB2-luc234R233 (Example 1) and Arr-TEV plasmids (Example 2) using appropriate commercial transfection kits. Forty-eight hours after transfection, cells were treated with or without 10 µM ADRB2 agonist, isoproterenol, for 2 hours, Bright-GLO™ or Steady-GLO™ (Promega) was added to the cells, and relative luminescence of the lysates was recorded by an appropriate luminescence reader. Over three-fold increase in luminescence activity was observed in the presence of isoproterenol.

Figure 5:
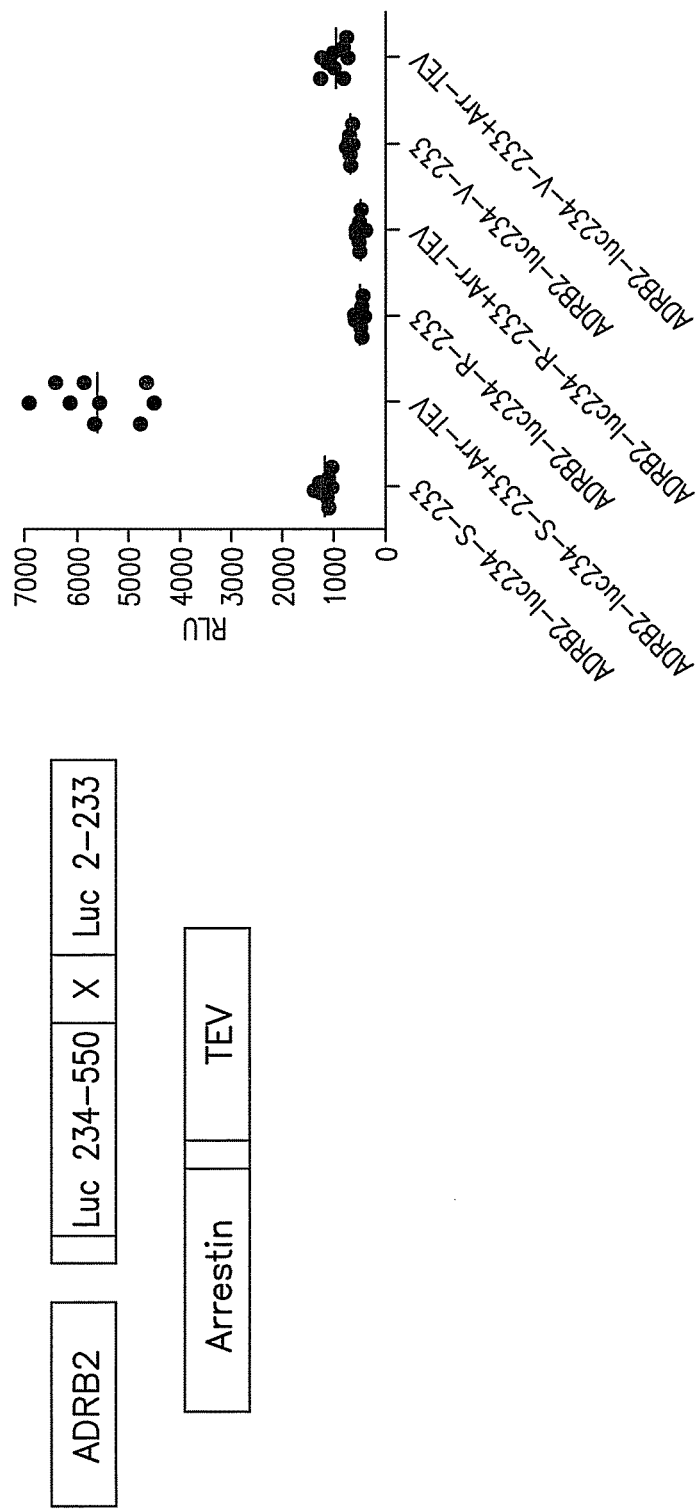
FIG. 5 shows that regenerated luciferase activity from permuted luciferase fusion proteins by TEV protease in cells can be controlled by modifying the protease cleavage site. Signal-to-noise ratio is thereby controllable. Two constructs are depicted, ADRB2 is the β2 adrenergic receptor, Luc 234-550 and 2-233 are the two fragments of luciferase linked by X, the TEV cleavage site with a variable C terminal amino acid. X can be serine, S, arginine, R, or valine, V, for example. The reconstituted luciferase activity was observed from a permuted luciferase fusion protein in mammalian cells when both constructs were present in a cell. Susceptibility to cleavage by TEV can depend on the specific residues of the cleavage site. RLU here and elsewhere indicates Relative Luminescence (or Light) Units. No ligand was used in the experiment.

FIG. 5 shows expression of GPCR/permuted luciferase with and without Arr2-TEVp. In the data represented in the graph, the constructs were introduced into cells, but the transfected cells were not exposed to any modulator. Thus, the data indicate that when the cleavage site contains serine, there is some spontaneous activity, but essentially no background noise arises when X is R or V. As noted in FIG. 6, when cells expressing the R or V cleavage site were exposed to agonist, a response was observed. FIG. 7 shows dose-dependent response of luciferase activity in cells transiently or stably expressing GPCR-luc234V233 and/or Arr-TEV.

Example 4

Figure 8:
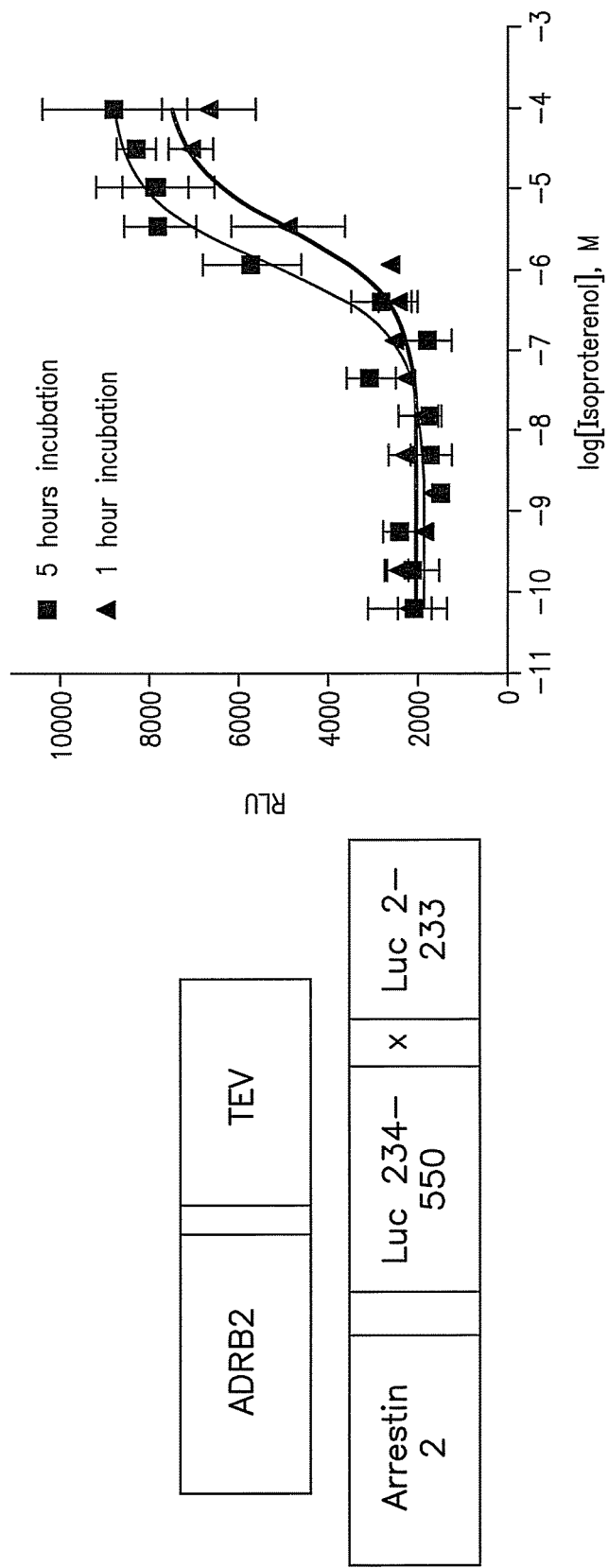
FIG. 8 shows an alternative GPCR-permuted luciferase assay. The expression constructs carried ADRB2 bound to the reporter activator and arrestin 2 bound to the protease. The constructs were transiently transfected into HEK 293 cells. The reaction kinetics are depicted in the graph with a one hour (▲) and a five hours (■) reaction incubation.

FIG. 8 shows that a 5 hour or a 1 hour incubation period is sufficient for assaying protein-protein interaction. A dose response relationship is clearly shown.

An ADRB2-TEV fusion gene expression plasmid was constructed by fusing tobacco etch virus protease A to the C terminus of ADRB2 and inserting the fusion gene into pcDNA3.1(+) with a zeocin selection marker (Invitrogen Cat #43-0018). All DNA fragments were generated by PCR using appropriate templates as known in the art.

The β arrestin 2-permuted luciferase (Arr-luc234X233) fusion gene expression plasmid was constructed by fusing permuted luciferase luc234X233 to the C terminus of β arrestin 2. The TEV protease cleavage site is ENLYFQ/X, (Rachel B. Kapust, et al. *Biochemical & Biophysical Research Communications*, 294 (2002) 949-955) where E and Q generally are invariant, and in which X can be any amino acid, although G and S are common amino acids found at that site. Cleavage occurs between the Q and the X residues. X can determine cleavage efficiency. In some embodiments, the TEV protease cleavage site was included in the permuted luciferase. Background and signal/noise ratio can be improved by simple routine experimentation. For example, use of a valine in place of glycine at the X hydrolysis site for TEV has been found to lower background in some applications. The fused fusion gene was cloned in pcDNA3.1(+) with a neomycin selection marker (Invitrogen).

HEK293 cells were cotransfected with plasmids ADRB2-TEV and Arr-luc234V233, where the TEV recognition sequence is ENLYFQV (SEQ ID NO:12), using appropriate commercial transfection kits. Forty-eight hours after transfection, cells were treated with different concentrations of ADRB2 agonist, isoproterenol, for 1 and 5 hours, Bright-GLO™ (Promega) was added to the cells, and the relative luminescence units were recorded on EnVision II™. Dose-dependent luminescence activity was observed after both 1 hour and 5 hours incubation with isoproterenol.

Example 5

Figure 9:
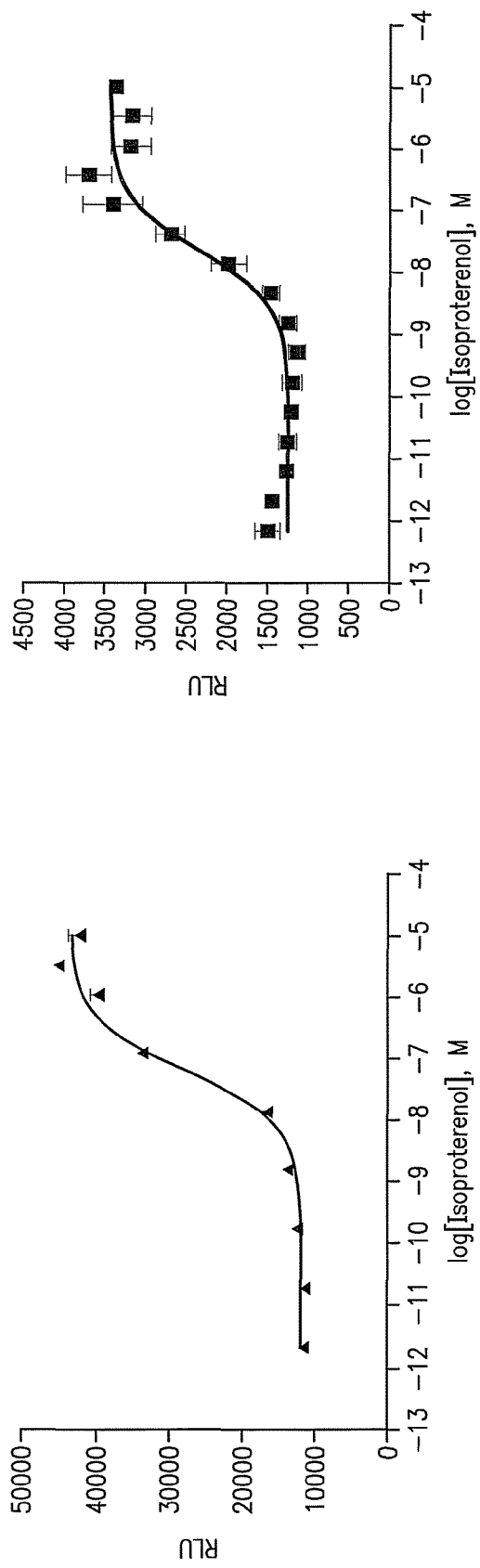
FIG. 9 depicts generation of a HEK cell line stably expressing an arrestin/permuted enzyme construct carrying V at the X site which was transiently transfected with receptor ADRB2-TEV (left graph) and a CHO cell line stably expressing Arr-luc234S233 and transiently transfected with the receptor-TEV construct.

FIG. 9, left panel shows ligand-induced luciferase activity in HEK293 cells stably expressing Arr-luc234V233 and transiently expressing ADRB2-TEV fusion proteins. The right panel shows stable expression of the arrestin-reporter activating protein construct and transient expression of the 7TMR-protease fusion in CHO cells.

Stable cell lines expressing GPCR-luc234R233 or Arr-TEV were generated in HEK293 or CHO cells. Twenty ng/well of each DNA were used for transfection in a 12-well plate with Lipofectamine (Invitrogen) for HEK293 and TranIT-CHO cells.

In the per-luc assay, a 384-well plate format was routinely used. Other plate formats were deemed acceptable formats. CHO cells stably expressing GPCR-luc234R233 or Arr-TEV were plated at 10,000 cells per well in a tissue culture-treated surface 384-well white assay plate (Becton Dickinson). The following day, cells were treated with agonist, concentrations from 10 µM to 0.7 µM (in 3:1 serial dilutions made in serum-free cell medium). Steady-Glo Luciferase Assay System (Promega) was used for measuring luciferase activity. After 2 hours of agonist treatment, medium was aspirated and 25 µl luciferase assay reagent were added to each well. Relative luminescence units (RLUs) were read on EnVision, a multi-label reader from Perkin Elmer. Data were plotted and analyzed with PRISM software.

HEK293 cells stably expressing Arr-luc234V233 were generated by selection for resistance to neomycin. The neomycin resistant gene is presented in the Arr-luc234V233 expression plasmid vector pcDNA3.1.

Example 6

FIG. 9, right panel shows a dose response to isoproterenol in a CHO line. Stable cell lines expressing GPCR-luc234R233 or Arr-TEV were generated in CHO cells. One µg of each DNA was used in the transfection per well in a 12-well plate with the TransfectIT-CHO transfection kit (Minis Bio, Madison, Wis.). Single colonies were harvested from transfectants under selection with neomycin or zeomycin.

The Arr-luc234V233 stable expressing cells were transfected with the ADRB2-TEV plasmid using appropriate commercial transfection kits. The cells transiently expressing ADRB2-TEV and stably expressing Arr-luc-234V233 were incubated with isoproterenol for two hours, and Bright- GLO™ luciferase reagent was added to cells. Dose-dependent luciferase activity was recorded on EnVison II.

Example 7

FIG. 10 shows an evaluation of the GPCR Per-Luc assay for agonist, partial agonist, antagonist, and non-specific endogenous receptor responses.

HEK293 cells stably expressing Arr-luc234V233 were transfected with ADRB2-TEV plasmid using Lipofectamine 2000 transfection reagent (Invitrogen). Forty-eight hours after transfection, cells were incubated with different concentrations of the known agonist, isoproterenol; partial agonist BRL37344 (Sigma-Aldrich); antagonist ICI118551 (ICI); antagonist ICI 118551 with 200 nM of isoproterenol; and agonist S1P (sphingosine-1-phosphate) for HEK293 endogenous EDG receptors for two hours, and Bright-GLO™ luciferase reagent was added to the cells. Dose-dependent luciferase activity was recorded on EnVison II, as shown in FIG. 10.

The EC50 and IC50 values of the assay were similar to values obtained in FLIPR and cAMP assays. Endogenous receptor EDG in HEK293 cells and its ligand S1P did not affect the luciferase activity, whereas other assays such as FLIPR and cAMP did produce positive signals. Isoproterenol, an agonist, generated a response. The partial agonist, BRL37344 presented a graded response. The antagonist, ICI18551, inhibited isoproterenol, but had no activity alone. Therefore, the instant assay is specific, and as shown in FIG. 10 (taken in conjunction with other comparative data) yields fewer and reduced false positive signals.

Example 8

Figure 14:
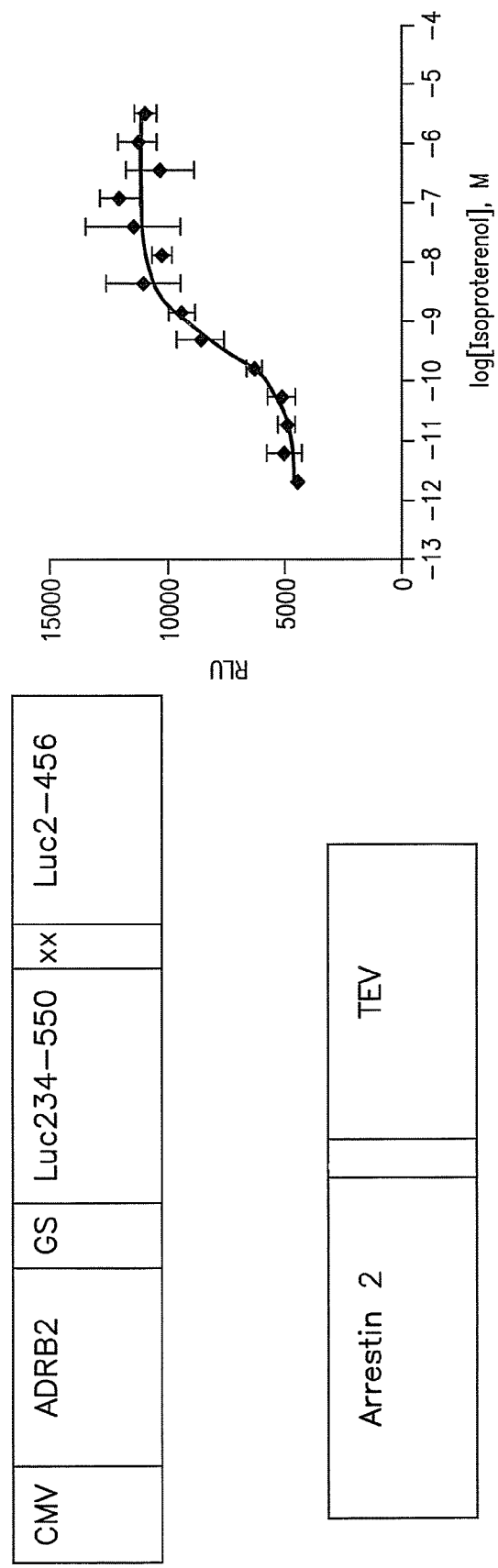
FIG. 14 depicts expression constructs that contain an overlap of essentially full length, but not complete copies of luciferase joined as taught herein to produce a permuted luciferase. CMV is a cytomegalovirus promoter. Luc2-456 and Luc234-550 are the essentially full length luciferase fragments. In this example, GS is a peptide linker composed of glycine and serine. The TEV cleavage site has a valine at the C-terminus.
Figure 15:
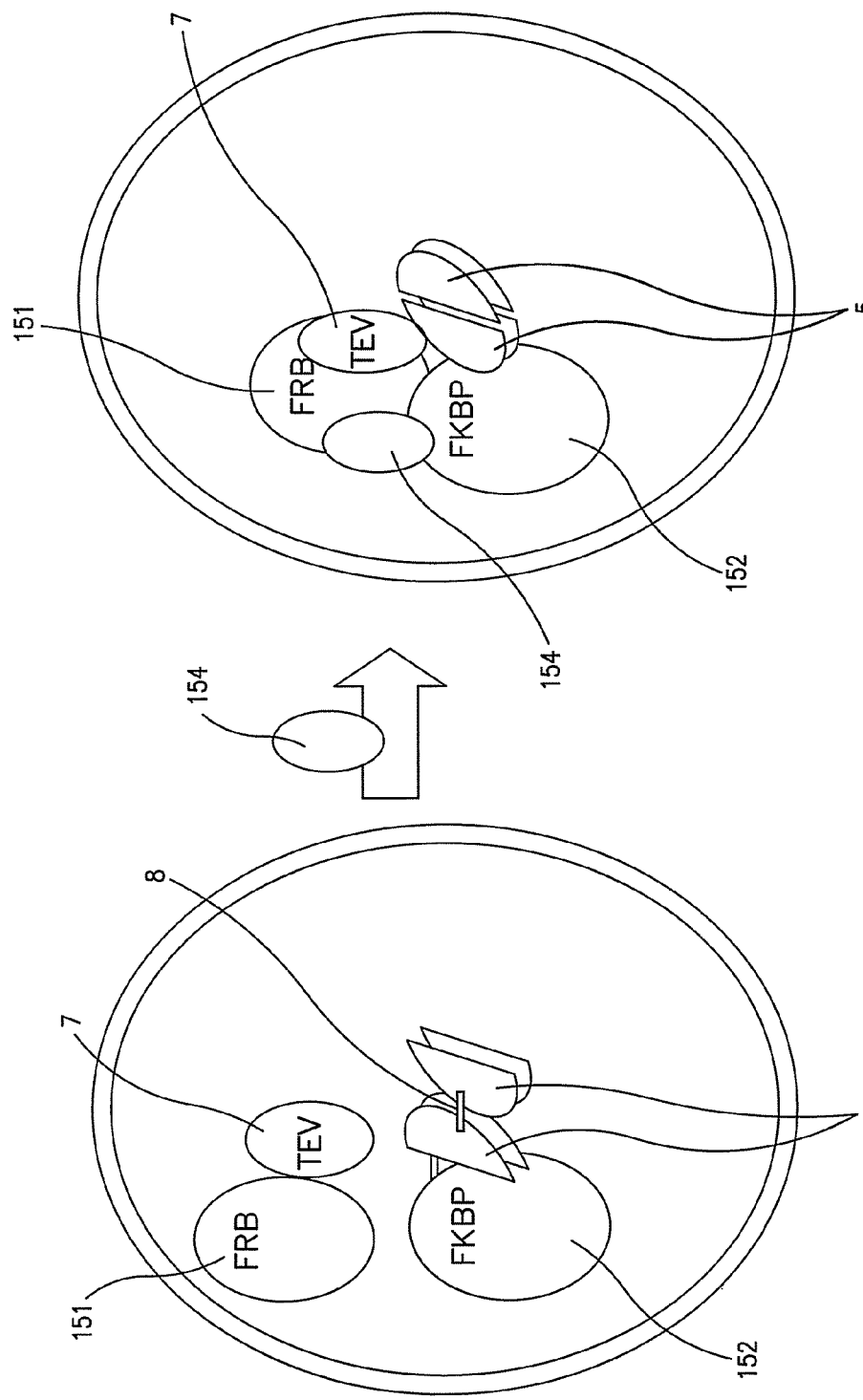
FIG. 15 shows an example of an assay to monitor intracellular protein-protein interactions. Rapamycin is an immunosuppressive drug that binds simultaneously to the rapamycin-binding protein (FKBP12, or FKBP) and the FKBP-rapamycin binding (FRB) domain of the mammalian target of rapamycin (mTOR) kinase. mTOR is a murine serine/threonine protein kinase comprising a rapamycin binding domain 151 which is a mammalian target of rapamycin 154. FKBP 152 is the 12 kDa FK506-binding protein, which has a rapamycin binding site. TEV protease is fused to the rapamycin binding domain of mTOR, FRB 151. The permuted reporter activating protein is fused to FKBP 152, the rapamycin binding domain of FKBP12. Rapamycin 154 reacts with, mediates the binding with and brings FRB 151 and FKBP 152 into proximity resulting in the permuted reporter activation.
Figure 16:
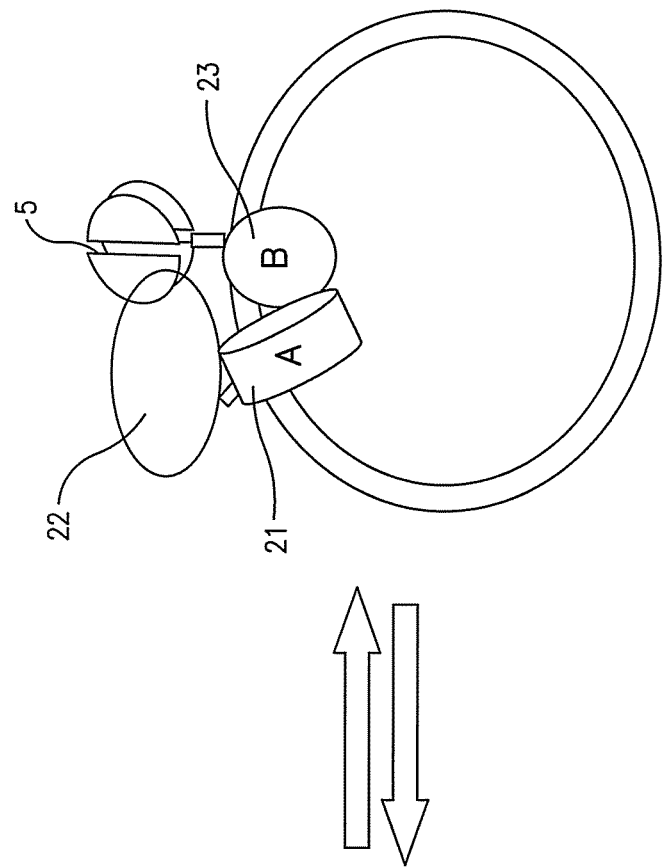
FIG. 16 depicts an assay configuration where proteins A 21 and B 23 are two membrane-bound receptors which dimerize (left to right) spontaneously or dissociate (right to left) upon binding ligand. The assay can monitor spontaneous interaction of the two receptors or induced interaction, where either or both receptors bind a ligand, which may be the same or different. Alternatively, proteins A 21 and B 23 may dimerize spontaneously or without having to bind a ligand or modulator (not shown). In this embodiment, the protease and permuted reporter activator portions of the fusion proteins are expressed at the cell surface or exterior of the artificial package or unit. The assay also can be configured to monitor disruption of interacted receptors, whether spontaneous or mediated by one or more molecules, as evidenced by a decay, diminution or loss of signal.
Figure 16:
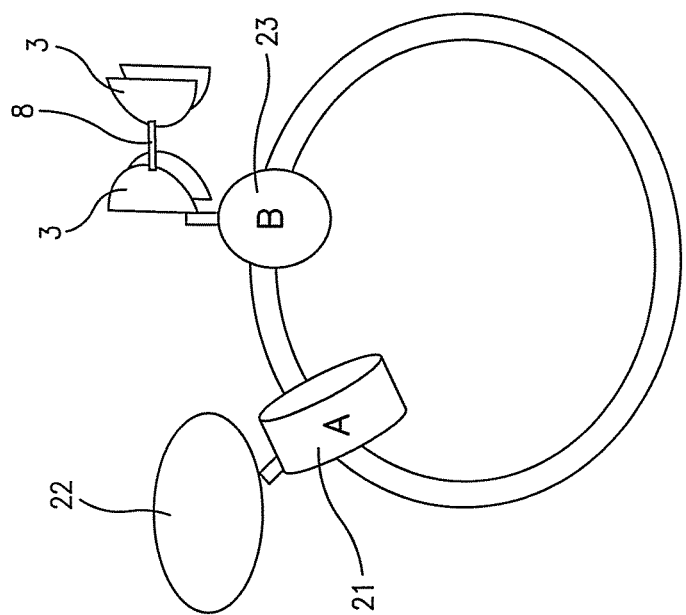
Figure 17:
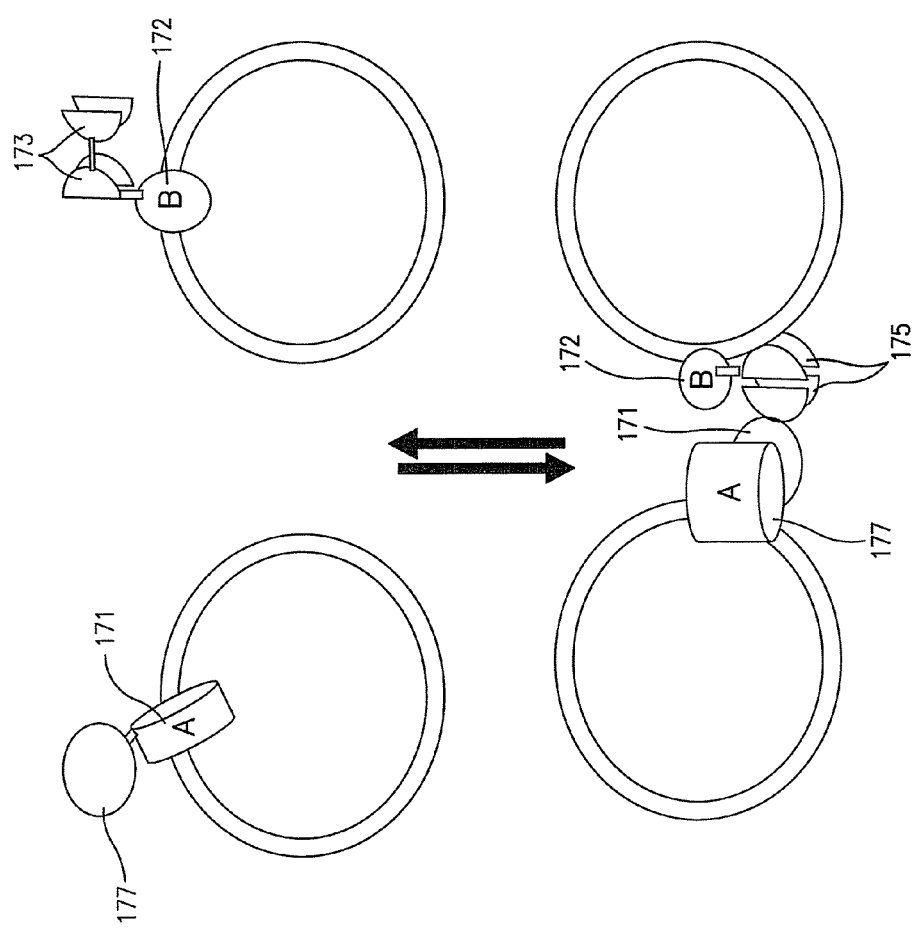
FIG. 17 depicts a cellular assay where proteins A 171 and B 172 reside in or on separate cells, which can bind, abut, interact and so on. Again, either A 171 or B 172 can carry the protease 177 or the permuted signal activating protein 173. The assay can detect spontaneous interaction of the two labeled receptors on the two cells or induced interaction where either or both receptors bind a ligand, which may be the same or different, as evidence of cell-cell interaction or proximity. In this embodiment, the protease 177 and permuted reporter activator portions 173 of the fusion proteins are expressed at the cell surface or exterior of the artificial package. The activated permuted reporter 175 results from the proteins A 171 and B 173 associating with one another. Alternatively, the receptor fusion and the intracellular protein fusion of interest can be present in one cell, and the inducing event, the ligand and so on that is being monitored is expressed on a second cell or is the second cell. The assay also can be configured to monitor disruption of interacted receptors and cells, whether spontaneous or mediated by one or more molecules, as evidenced by a decay, diminution or loss of signal as the cells separate.

FIG. 14 shows an example where a permuted luciferase was constructed by cloning firefly luciferase N terminal amino acids 2 to 456 behind C terminal amino acids 234 to 550 with a TEV protease recognition site, ENLYFQX, using V for X. The permuted luciferase (luc234V456) was fused to the C terminus of the GPCR, ADRB2, to generate the GPCR-permuted luciferase construct, ADRB2-luc234V456 expression plasmid.

All DNA fragments were generated by PCR using appropriate templates. ADRB2-luc234V456 fusion genes were cloned in pcDNA3.1(+) with a neomycin selection marker (Invitrogen).

CHO-K1 cells were co-transfected with ADRB2-luc234V456 and Arr-TEV plasmids using appropriate commercial transfection kits. Forty-eight hours after transfection, cells were treated with or without 10 μM ADRB2 agonist, isoproterenol, for 2 hours, Bright-GLO™ or Steady-GLO™ (Promega) was added to the cells, and relative luminescence was recorded by appropriate luminescence readers. Reconstituted luciferase activity was observed in response to different doses of isoproterenol.

HEK293 cells stably expressing Arr-luc234V233 were selected for resistance to neomycin. The neomycin resistant gene is presented in the Arr-luc234V233 expression plasmid vector pcDNA3. Luciferase activity in response to agonist was observed.

Example 9

Figure 13:
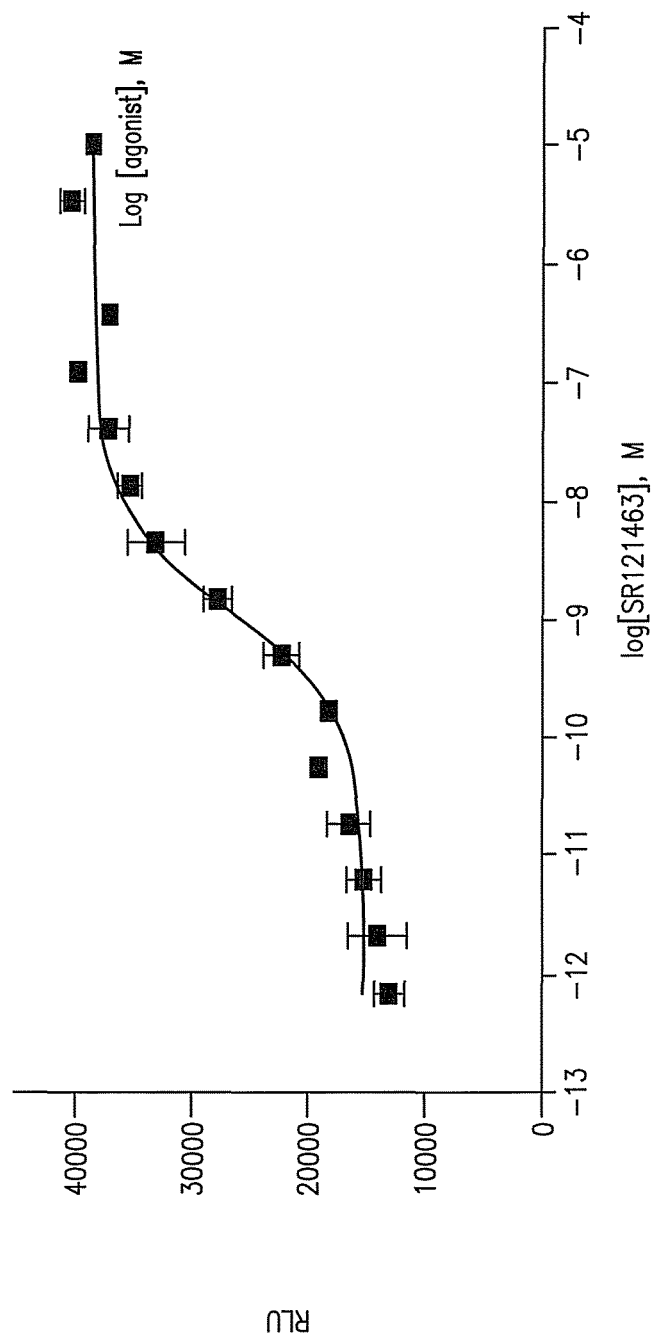
FIG. 13 shows a β arrestin-based assay for V2. In the graph, a V2 inverse agonist (SR121463) induced a G protein-independent, arrestin-dependent signal.

FIG. 13 shows dose dependency with V2 inverse agonist. For this example, HEK293 cells stably expressing Arr-luc234V233 were transfected with V2-TEV plasmid using Lipofectamine 2000 transfection reagent (Invitrogen). Forty-eight hours after transfection, the cells were incubated with different concentrations of a compound, SR121463 (sanofi Recherché, Toulouse, F R), considered an antagonist using standard assays, for two hours. Bright-GLO™ luciferase reagent was added to cells. Dose-dependent luciferase activity was recorded on EnVison II. That is increasing levels of luminescence were observed with increasing amounts of SR121463, more properly defined an inverse agonist.

In this assay, inverse agonist behaved as an agonist, as do other inverse agonists. It is known that an inverse agonist can block the V2 G protein signal pathway, while promoting β arrestin-mediated activation of MAPK (Azzi et al., PNAS, 2003, 100:11406-11411). So the assay of the present invention can indicate distinct active conformations for G protein-coupled receptors.

In contrast, in classical assay systems, inverse agonists of GPCRs behave as antagonists. This is because inverse agonists probably bind to and stabilize the inactive conformation of GPCR for G protein signaling. However, some inverse agonists both stabilize the inactive form of GPCR for G protein signaling and also promote β arrestin recruitment to the GPCR to activate a β arrestin signaling pathway.

Example 10

Figure 6:
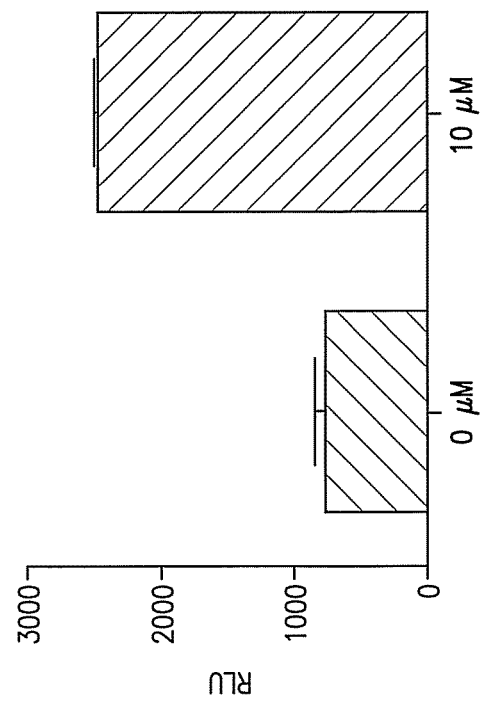
FIG. 6 shows agonist-induced luciferase activity in a GPCR-permuted luciferase cell-based assay using the ADBR2 receptor attached to a permuted luciferase with different TEV protease cleavage sites, R at the X position of the TEV cleavage site (left graph) and V at the X position (right graph). TEV protease was fused to arrestin. The x-axis of each graph shows a zero value (no agonist) and 10 µM agonist.
Figure 6:
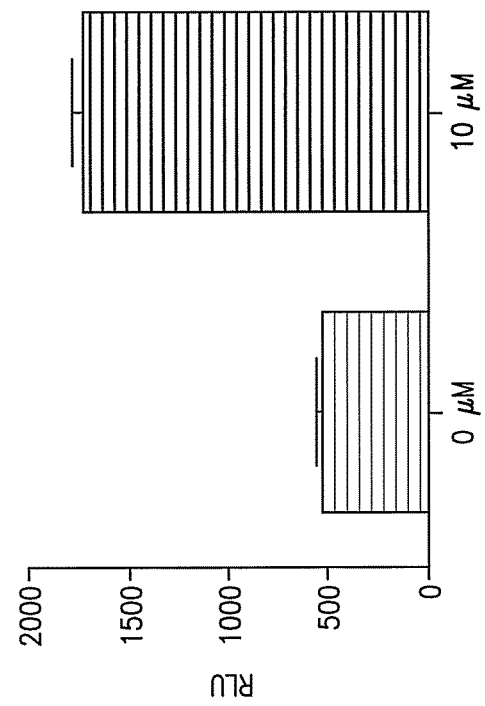
Figure 7:
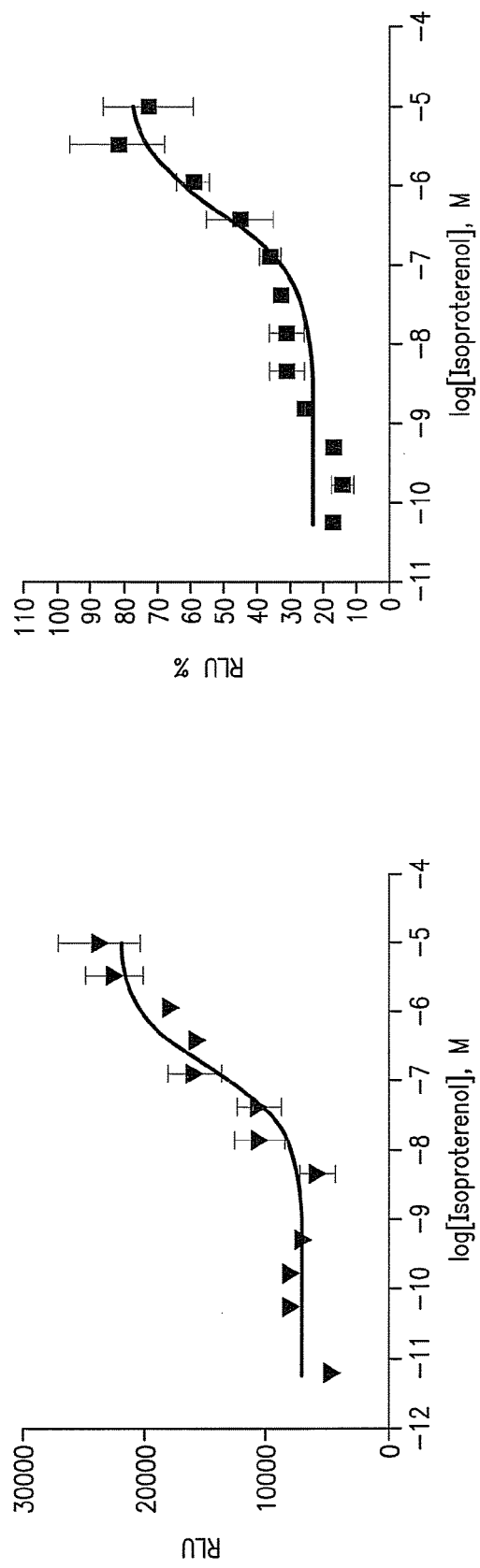
FIG. 7 shows a dose-dependent response of luciferase activity in a GPCR-permuted luciferase cell-based assay in cotransiently transfected and partial transiently transfected systems. In the left graph, the valine at the protease cleavage site construct was used in CHO cells. Both the ADRB2-luc and Arr-TEV constructs were transiently cotransfected. In the right graph, the cells were stably transfected with the R-containing luciferase construct fused to ADRB2 which were then transiently transfected with the Arr-TEV construct.

FIG. 6 shows agonist-induced luciferase activity.

In this example, permuted luciferase was constructed by rearranging firefly luciferase N terminal amino acid 2 to 233 and C terminal amino acid 234 to 550 in reverse order, interrupted by a TEV protease recognition site, ENLYFQX. The position X can be any amino acid. Amino acids at this position are known to dictate TEV protease recognition affinity and cleavage efficiency. The permuted luciferase (luc234X233) was then fused to the C terminus of the GPCR, i.e., ADRB2, to generate a GPCR-permuted luciferase, i.e., the ADRB2-luc234X233 expression plasmid.

Human β arrestin 2-TEV fusion plasmid was constructed by fusing tobacco etch virus protease A to the C terminal of β arrestin 2. DNA fragments were generated by PCR using appropriate templates. GPCR-luc234X233 fusion genes were subcloned in pcDNA3.1(+) with a neomycin selection marker (Invitrogen) and Arr-TEV fusion gene was subcloned in pcDNA3.1(+) with a zeocin selection marker (Invitrogen Cat #43-0018).

CHO-K1 cells were co-transfected with ADRB2-luc234R233 and Arr-TEV plasmids using appropriate commercial transfection kits. Forty-eight hours after transfection, cells were treated with or without 10 μM of ADRB2 agonist, isoproterenol, for 2 hours, Bright-GLO™ or Steady-GLO™ (Promega) was added to the cells, and relative luminescence was recorded by appropriate luminescence readers. Over a three-fold increase in luminescence activity was observed in the presence of isoproterenol.

Example 11

Figure 12:
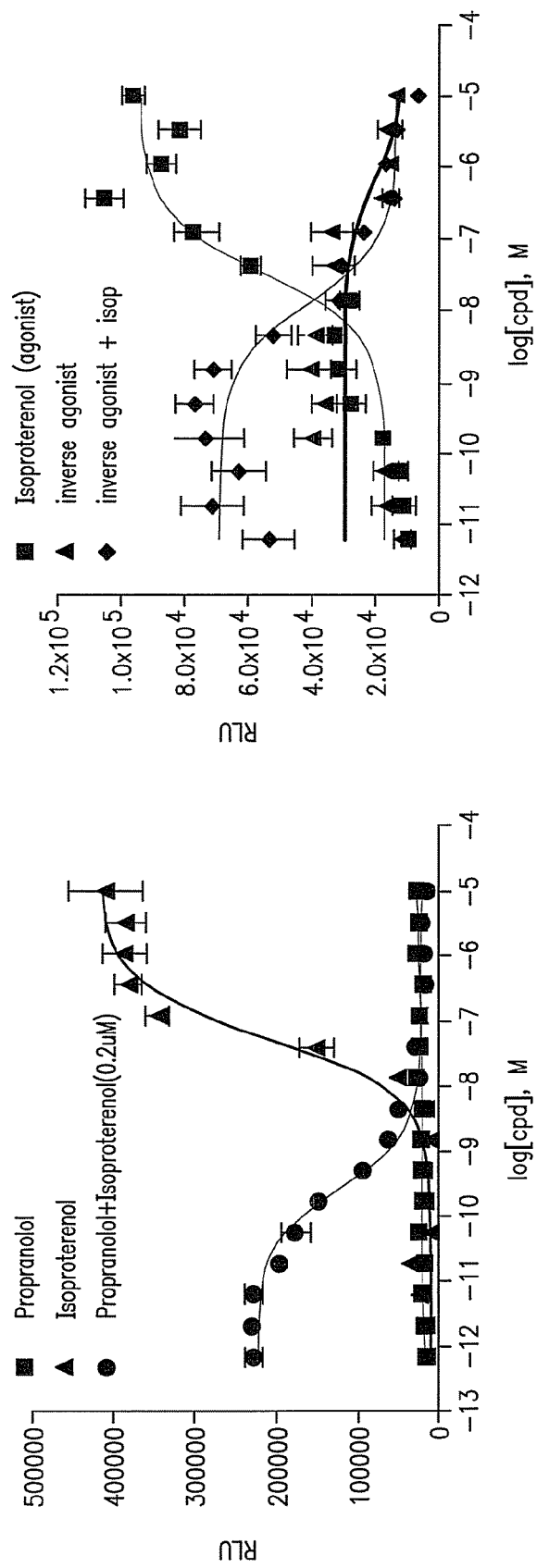
FIG. 12 shows several β arrestin-based assays for ADRB2. In the graph on the right, DiscoveRX HEK cells were transiently transfected with ADRB2 as per the manufacturer's instructions and tested with an antagonist (propranolol) (■), agonist isoproterenol) (▲) and a combination thereof (●) on the left and on the right with an agonist (■), an inverse agonist (▲), right) and a combination thereof (●). The assay shown at right was compared to the instant assay for response to an antagonist, the isoproterenol agonist and a combination thereof (left graph). The instant assay at left provided greater discrimination and higher specific activity.

FIG. 12 shows results of agonists, antagonists and inverse agonists using the present invention (Left Panel) and another assay (Right Panel). The two plots show differentiation and counter effects of agonist, antagonist and inverse agonist. The instant assay provides good specific activity.

Example 12

FIG. 7 shows CHO cells with both ADRB2-permuted luciferase and Arr-TEV. The data of the left panel, ADRB2-luc234V233 was made to contain the TEV recognition site, ENLYFQV. CHO-K1 cells were cotransfected with ADRB2-luc234V233 and Arr-TEV plasmids using appropriate commercial transfection kits. Forty-eight hours after transfection, cells were treated with different concentrations of ADRB2 agonist isoproterenol for 2 hours, Bright-GLO™ or Steady-GLO™ (Promega) was added to the cells, and relative luminescence was recorded by appropriate luminescence readers.

Example 13

FIG. 7, the right panel summarizes data using stably transfected cells with different cleavage sites. The results are similar to that of the left panel. Hence, two GPCR-luciferase constructs having different cleavage sites responded to agonist.

Example 14

FIG. 6 shows agonist-induced signal activity comparing X as R and X as V. The results are similar showing that X can be routinely varied.

In this example, permuted luciferase was constructed by rearranging firefly luciferase N terminal amino acids 2 to 233 and C terminal amino acids 233 to 550 in reverse order, interrupted by a TEV protease recognition site, ENLYFQ/X. The position X can be any amino acid that dictates TEV protease recognition affinity and cleavage efficiency. V and R are shown. The permuted luciferase (luc234X233) was then fused to the C terminus of the GPCR, i.e., ADRB2, to generate the GPCR-permuted luciferase, i.e. ADRB2-luc234X233 expression plasmid.

In this example, human βb arrestin 2-TEV fusion plasmid was constructed by fusing tobacco etch virus protease A to the C terminus of β arrestin 2. All DNA fragments were generated by PCR using appropriate templates. GPCR-luc234X233 fusion genes were subcloned in pcDNA3.1(+) with a neomycin selection marker (from Invitrogen) and the Arr-TEV fusion gene was subcloned in pcDNA3.1(+) with a zeocin selection marker (Invitrogen Cat. #43-0018).

CHO-K1 cells were cotransfected with the ADRB2-luc234R233 and Arr-TEV plasmids using appropriate commercial transfection kits. After 48 hours, cells were treated with or without 10 µM of ADRB2 agonist for 2 hours, Bright-GLO™ or Steady-GLO™ (Promega) was added to the cells, and relative luminescence units were recorded by appropriate luminescence readers. Over three-fold higher levels of luminescence activity was observed in the presence of isoproterenol.

Example 15

Figure 11:
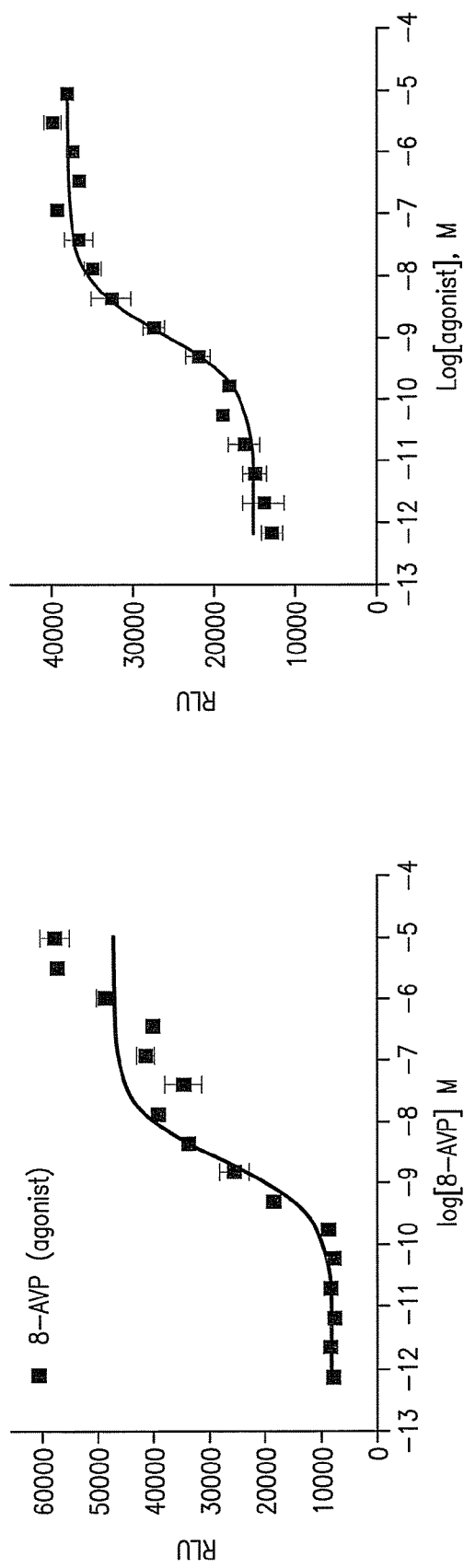
FIG. 11 shows an evaluation of a GPCR Per-Luc assay with V2 (vasopressin receptor 2) agonist and inverse agonist. HEK cells stably transfected with an arrestin/permuted luciferase construct were transiently transfected with a V2-TEV construct and induced with the agonist, 8AVP, arginine vasopressin (left graph). When those cells were tested with an inverse agonist, a dose dependency was observed, with the signal mediated by arrestin rather than a G protein (right graph).

FIG. 11, the left panel shows results with 8-AVP agonist in cells transiently expressing V2-TEV.

In this example, HEK293 cells stably expressing Arr-luc234V233 were transfected with V2-TEV plasmid using Lipofectamine 2000 transfection reagent (Invitrogen). After 48 hours, the cells were incubated with different concentrations of agonist 8-AVP (Arg$^8$ vasopressin, a known agonist of the V2 vasopressin receptor) for two hours, and Bright-GLO™ luciferase reagent was added to cells. Dose-dependent luciferase activity was recorded on EnVison II.

Example 16

HEK293 cells stably expressing Arr-luc234V233 were transfected with V2-TEV plasmid using Lipofectamine 2000 transfection reagent (Invitrogen). After 48 hours, the cells were incubated with different concentrations of inverse agonist for two hours, and Bright-GLO™ luciferase reagent was added to cells. Dose-dependent luciferase activity was recorded on EnVison II.

In this assay, the inverse agonist behaves as an agonist. It is known that some inverse agonists block a V2 G-protein signal pathway, but promote β arrestin-mediated activation of MAPK (Azzi et al., *PNAS*, 2003 100:11406-11411). So the assay can assess distinct active conformations of G protein-coupled receptors.

Example 17

FIG. 11, the right panel shows V2 inverse agonist-produced dose-dependent luciferase activity by promoting β arrestin interaction with a V2 receptor.

In this example, HEK293 cells stably expressing Arr-luc234V233 were transfected with V2-TEV plasmid using Lipofectamine 2000 transfection reagent (Invitrogen). After 48 hours, the cells were incubated with different concentration of inverse agonist for two hours, and Bright-GLO™ luciferase reagent was added to the cells. Dose-dependent luciferase activity was recorded on EnVison II.

Other features of the invention will be clear to the skilled artisan and need not be reiterated here. The artisan can make various modifications without departing from the spirit and scope of the instant invention.

All references cited herein are herein incorporated by reference in entirety.

---

The invention claimed is:

1. A method to identify a compound that modulates a protein-protein interaction between a first protein and a second protein comprising:
   i) providing a first protein that is attached to a reporter activating protein that is arranged to be inactive, wherein the inactive reporter activating protein comprises a cleavage site for a protease that is interposed between two portions of the inactive reporter activating protein;
   ii) providing a second protein that is attached to a protease, wherein the protease is capable of cleaving the cleavage site in the inactive reporter activating protein;
   iii) providing a reporter whose signal is altered by the activity of an active reporter activating protein;
   iv) providing a test compound;
   v) reacting the test compound with the first protein, the second protein, and the reporter, causing the first protein to associate with the second protein, which association causes the protease to cleave the inactive reporter activating protein at the cleavage site, resulting in the two portions of the inactive reporter activating protein to be rearranged to be active and generate the active reporter activating protein, causing the active reporter activating protein to activate the reporter; and
   vi) measuring the signal generated by the activated reporter;

wherein a change in the signal is indicative of the protein-protein interaction between the first protein and second protein.

2. The method of claim 1, wherein the first protein forms a fusion protein with the reporter activating protein.

3. The method of claim 1, wherein the method further comprises providing a molecule known to modulate the protein-protein interaction, wherein the test compound modulates interaction of the molecule with the protein-protein interaction.

4. The method of claim 1, wherein the reporter activating protein is an enzyme.

5. The method of claim 1, wherein the reporter activating protein is a protein that causes a change of fluorescence of the reporter.

6. The method of claim 1, wherein at least one of the first protein and second protein is a membrane bound protein.

7. The method of claim 1, wherein at least one of the first protein and second protein is a cytoplasmic protein.

8. The method of claim 1, wherein at least one of the first protein and second protein is modified in order to increase the binding affinity of the first or second protein to the other protein.

9. The method of claim 1, wherein the first protein is selected from the group consisting of: a G-protein coupled receptor, a β-adrenergic receptor, an arginine vasopressin receptor 2, a serotonin receptor 1a, a m2 muscarinic acetylcholine receptor, a chemokine receptor 5, a dopamine D2 receptor, a kappa opioid receptor, an α1a-adrenergic receptor, an insulin growth factor-1 receptor, an estrogen receptor 1, an estrogen receptor 2, a frizzled receptor, an epidermal growth factor receptor, a receptor tyrosine kinase, a receptor serine/threonine kinase, a transforming growth factor-β receptor, an activin, a bone morphogenetic protein receptor, a cytokine receptor, an interferon receptor, an interleukin receptor, a erythropoietin receptor, a tumor necrosis factor receptor, a leptin receptor, a granulocyte colony stimulating factor receptor, or a granulocyte-macrophage colony stimulating factor receptor.

10. The method of claim 1, wherein the second protein is selected from the group consisting of: arrestin, and Dishevelled binding protein.

11. The method of claim 1, wherein the protease is selected from the group consisting of: a tobacco etch virus nuclear inclusion A (TEV) protease, an enterokinase, a factor Xa protease, a thrombin, a protease with a five residue recognition sequence, a protease with a six residue recognition sequence, a protease with a seven residue recognition sequence, a serine/threonine protease, a thiol protease, an aspartic protease, a metalloproteinase, an aminopeptidase, a dipeptidase, a tripeptidase, a carboxypeptidase, and a peptidyl peptidase.

12. The method of claim 1, wherein the reporter activating protein is selected from the group consisting of: a luciferase, a Gaussia luciferase, a renilla luciferase, a peroxidase, a β-galactosidase, or a β-lactamase.

13. The method of claim 1, wherein the reporter is selected from the group consisting of: a galactosidase substrate, a peroxidase substrate, a luciferase substrate, and luciferin.

14. The method of claim 1, wherein the reporter signal is selected from the group consisting of: luminescence, and a color change.

15. The method of claim 1, wherein the protein-protein interaction requires translocation of the first protein or second protein to a cellular compartment or organelle.

16. A method to identify a compound that modulates a protein-protein interaction between a first protein and a second protein comprising:
   i) providing a first protein that is attached to a reporter that is arranged to be inactive, wherein the inactive reporter comprises a cleavage site for a protease that is interposed between two portions of the inactive reporter;
   ii) providing a second protein that is attached to a protease, wherein the protease is capable of cleaving the cleavage site in the inactive reporter;
   iii) providing a test compound;
   iv) reacting the test compound with the first protein and the second protein, causing the first protein to associate with the second protein, which association causes the protease to cleave the inactive reporter at the cleavage site, resulting in the two portions of the inactive reporter to be rearranged to be active and generate the active reporter; and
   vi) measuring the signal generated by the active reporter; wherein a change in the signal is indicative of the protein-protein interaction between the first protein and the second protein.

17. The method of claim 16, wherein the first protein forms a fusion protein with the reporter.

18. The method of claim 16, wherein at least one of the first protein and second protein is a membrane bound protein.

19. The method of claim 16, wherein at least one of the first protein and second protein is a cytoplasmic protein.

20. The method of claim 16, wherein at least one of the first protein and second protein is modified in order to increase its binding affinity to the other protein.

21. The method of claim 16, wherein the first protein is selected from the group consisting of: a G-protein coupled receptor, a β-adrenergic receptor, an arginine vasopressin receptor 2, a serotonin receptor 1a, a m2 muscarinic acetylcholine receptor, a chemokine receptor 5, a dopamine D2 receptor, a kappa opioid receptor, an α1a-adrenergic receptor, an insulin growth factor-1 receptor, an estrogen receptor 1, an estrogen receptor 2, a frizzled receptor, an epidermal growth factor receptor, a receptor tyrosine kinase, a receptor serine/threonine kinase, a transforming growth factor-β receptor, an activin, a bone morphogenetic protein receptor, a cytokine receptor, an interferon receptor, an interleukin receptor, a erythropoietin receptor, a tumor necrosis factor receptor, a leptin receptor, a granulocyte colony stimulating factor receptor, or a granulocyte-macrophage colony stimulating factor receptor.

22. The method of claim 16, wherein the second protein is selected from the group consisting of: arrestin, and Dishevelled binding protein.

23. The method of claim 16, wherein the protease is selected from the group consisting of: a tobacco etch virus nuclear inclusion A (TEV) protease, an enterokinase, a factor Xa protease, a thrombin, a protease with a five residue recognition sequence, a protease with a six residue recognition sequence, a protease with a seven residue recognition sequence, a serine/threonine protease, a thiol protease, an aspartic protease, a metalloproteinase, an aminopeptidase, a dipeptidase, a tripeptidase, a carboxypeptidase, and a peptidyl peptidase.

24. The method of claim 16, wherein the reporter is selected from the group consisting of: a fluorescent protein, a green fluorescent protein, and a DsRed protein.

25. The method of claim 16, wherein the reporter signal is a color change.

26. The method of claim 16, wherein the protein-protein interaction requires translocation of the first protein or second protein to a cellular compartment or organelle.

* * * * *

UNITED STATES PATENT AND TRADEMARK OFFICE
CERTIFICATE OF CORRECTION

| | | |
|---|---|---|
| PATENT NO. | : 8,574,865 B2 | Page 1 of 1 |
| APPLICATION NO. | : 12/676284 | |
| DATED | : November 5, 2013 | |
| INVENTOR(S) | : Wright et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 585 days.

Signed and Sealed this
Twelfth Day of May, 2015

Michelle K. Lee
*Director of the United States Patent and Trademark Office*

SEQUENCE LISTING

<160> NUMBER OF SEQ ID NOS: 15

<210> SEQ ID NO 1
<211> LENGTH: 27
<212> TYPE: DNA
<213> ORGANISM: Tobacco etch virus

<400> SEQUENCE: 1
ggatccgcag agttgatcat catagtc                                         27

<210> SEQ ID NO 2
<211> LENGTH: 31
<212> TYPE: DNA
<213> ORGANISM: Tobacco etch virus

<400> SEQUENCE: 2
gggcccctat tgcgagtaca ccaattcatt c                                    31

<210> SEQ ID NO 3
<211> LENGTH: 7
<212> TYPE: PRT
<213> ORGANISM: Tobacco etch virus
<220> FEATURE:
<221> NAME/KEY: SITE
<222> LOCATION: (7)..(7)
<223> OTHER INFORMATION: Peptides that alter TEV protease reconition.
      X is S, R or V in FIgure 5.

<400> SEQUENCE: 3

Glu Asn Leu Tyr Phe Gln Xaa
1               5

<210> SEQ ID NO 4
<211> LENGTH: 1237
<212> TYPE: DNA
<213> ORGANISM: Human adenovirus type 1

<400> SEQUENCE: 4
gggcaacccg ggaacggcag cgccttcttg ctggcaccca atagaagcca tgcgccggac      60
cacgacgtca cgcagcaaag ggacgaggtg tgggtggtgg gcatgggcat cgtcatgtct     120
ctcatcgtcc tggccatcgt gtttggcaat gtgctggtca tcacagccat gccaagttc      180 gagcgtctgc agacggtcac caactacttc atcacttcac tggcctgtgc tgatctggtc     240
atgggcctgg cagtggtgcc ctttggggcc gcccatattc ttatgaaaat gtggactttt     300
ggcaacttct ggtgcgagtt tggacttcc attgatgtgc tgtgcgtcac ggccagcatt     360
gagaccctgt gcgtgatcgc agtggatcgc tactttgcca ttacttcacc tttcaagtac     420
cagagcctgc tgaccaagaa taaggcccgg gtgatcattc tgatggtgtg gattgtgtca     480
ggccttacct ccttcttgcc cattcagatg cactggtacc gggccaccca ccaggaagcc     540
atcaactgct atgccaatga gacctgctgt gacttcttca cgaaccaagc ctatgccatt     600
gcctcttcca tcgtgtccttt ctacgttccc ctggtgatca tggtcttcgt ctactccagg     660
gtctttcagg aggccaaaag gcagctccag aagattgaca atctgagggg ccgcttccat     720
gtccagaacc ttagccaggt ggagcaggat gggcggacgg gcatggact ccgcagatct     780 tccaagttct gcttgaagga gcacaaagcc ctcaagacgt taggcatcat catgggcact     840
ttcaccctct gctggctgcc cttcttcatc gttaacattg tgcatgtgat ccaggataac     900
ctcatccgta aggaagttta catcctccta aattggatag ctatgtcaa ttctggtttc     960 aatcccctta tctactgccg gagcccagat ttcaggattg ccttccagga gcttctgtgc    1020
ctgcgcaggt cttctttgaa ggcctatggg aatggctact ccagcaacgg caacacaggg    1080
gagcagagtg gatatcacgt ggaacaggag aaagaaaata aactgctgtg tgaagacctc    1140
ccaggcacgg aagactttgt ggccatcaa ggtactgtgc ctagcgataa cattgattca    1200
caagggagga attgtagtac aaatgactca ctgctgg                             1237

<210> SEQ ID NO 5
<211> LENGTH: 1110
<212> TYPE: DNA
<213> ORGANISM: homo sapiens

<400> SEQUENCE: 5
ctcatggcgt ccaccacttc cgctgtgcct gggcatccct ctctgccag cctgccagc       60

```
aacagcagcc aggagaggcc actggacacc cgggacccgc tgctagcccg ggcggagctg      120
gcgctgctct ccatagtctt tgtggctgtg gccctgagca atggcctggt gctggcggcc      180
ctagctcggc ggggccggcg gggccactgg gcacccatac acgtcttcat tggccacttg      240
tgcctggccg acctggccgt ggctctgttc caagtgctgc cccagctggc ctggaaggcc      300
accgaccgct tccgtgggcc agatgccctg tgtcgggccg tgaagtatct gcagatggtg      360
ggcatgtatg cctcctccta catgatcctg gccatgacgc tggaccgcca ccgtgccatc      420
tgccgtccca tgctggcgta ccgccatgga agtggggctc actggaaccg gccggtgcta      480
gtggcttggg ccttctcgct ccttctcagc ctgcccagc tcttcatctt cgcccagcgc      540
aacgtggaag gtggcagcgg ggtcactgac tgctgggcct gctttgcgga gccctggggc      600
cgtcgcacct atgtcacctg gattgccctg atggtgttcg tggcacctac cctgggtatc      660
gccgcctgcc aggtgctcat cttccgggag attcatgcca gtctggtgcc agggccatca      720
gagaggcctg gggggcgccg caggggacgc cggacaggca gccccggtga gggagcccac      780
gtgtcagcag ctgtggccaa gactgtgagg atgacgctag tgattgtggt cgtctatgtg      840
ctgtgctggg cacccttctt cctggtgcag ctgtgggccg cgtgggaccc ggaggcacct      900
ctggaagggg cgccctttgt gctactcatg ttgctggcca gcctcaacag ctgcaccaac      960
ccctggatct atgcatcttt cagcagcagc gtgtcctcag agctgcgaag cttgctctgc     1020
tgtgcccggg gacgcacccc acccagcctg ggtccccaag atgagtcctg caccaccgcc     1080
agctcctccc tggccaagga cacttcatcg                                      1110

<210> SEQ ID NO 6
<211> LENGTH: 951
<212> TYPE: DNA
<213> ORGANISM: Artificial
<220> FEATURE:
<223> OTHER INFORMATION: luciferase

<400> SEQUENCE: 6
gatactgcga ttttaagtgt tgttccattc catcacggtt ttggaatgtt tactacactc       60
ggatatttga tatgtggatt tcgagtcgtc ttaatgtata gatttgaaga agagctgttt      120
ctgaggagcc ttcaggatta caagattcaa agtgcgctgc tggtgccaac cctattctcc      180
ttcttcgcca aaagcactct gattgacaaa tacgatttat ctaatttaca cgaaattgct      240
tctggtggcg ctcccctctc taaggaagtc ggggaagcgg ttgccaagag gttccatctg      300
ccaggtatca ggcaaggata tgggctcact gagactacat cagctattct gattacaccc      360
gagggggatg ataaaccggg cgcggtcggt aaagttgttc cattttttga agcgaaggtt      420
gtggatctgg ataccgggaa aacgctgggc gttaatcaaa gaggcgaact gtgtgtgaga      480
ggtcctatga ttatgtccgg ttatgtaaac aatccggaag cgaccaacgc cttgattgac      540
aaggatggat ggctacattc tggagacata gcttactggg acgaagacga acacttcttc      600
atcgttgacc gcctgaagtc tctgattaag tacaaaggct atcaggtggc tcccgctgaa      660
ttggaatcca tcttgctcca acaccccaac atcttcgacg caggtgtcgc aggtcttccc      720
gacgatgacg ccggtgaact tcccgccgcc gttgttgttt tggagcacgg aaagacgatg      780
acggaaaaag agatcgtgga ttacgtcgcc agtcaagtaa caaccgcgaa aaagttgcgc      840
ggaggagttg tgtttgtgga cgaagtaccg aaaggtctta ccggaaaact cgacgcaaga      900
aaaatcagag agatcctcat aaaggccaag aagggcggaa agatcgccgt g              951
```

```
<210> SEQ ID NO 7
<211> LENGTH: 696
<212> TYPE: DNA
<213> ORGANISM: Artificial
<220> FEATURE:
<223> OTHER INFORMATION: luciferase

<400> SEQUENCE: 7
gaagacgcca aaaacataaa gaaaggcccg gcgccattct atccgctgga agatggaacc      60
gctggagagc aactgcataa ggctatgaag agatacgccc tggttcctgg aacaattgct     120
tttacagatg cacatatcga ggtggacatc acttacgctg agtacttcga aatgtccgtt     180
cggttggcag aagctatgaa acgatatggg ctgaatacaa atcacagaat cgtcgtatgc     240
agtgaaaact ctcttcaatt ctttatgccg gtgttgggcg cgttatttat cggagttgca     300
gttgcgcccg cgaacgacat ttataatgaa cgtgaattgc tcaacagtat gggcatttcg     360
cagcctaccg tggtgttcgt ttccaaaaag gggttgcaaa aattttgaa cgtgcaaaaa      420 aagctcccaa tcatccaaaa aattattatc atggattcta aaacggatta ccagggattt     480
cagtcgatgt acacgttcgt cacatctcat ctacctcccg gttttaatga atacgatttt     540
gtgccagagt ccttcgatag ggacaagaca attgcactga tcatgaactc ctctggatct     600
actggtctgc ctaaaggtgt cgctctgcct catagaactg cctgcgtgag attctcgcat     660
gccagagatc ctattttggg caatcaaatc attccg                               696

<210> SEQ ID NO 8
<211> LENGTH: 1363
<212> TYPE: DNA
<213> ORGANISM: Artificial
<220> FEATURE:
<223> OTHER INFORMATION: luciferase

<400> SEQUENCE: 8
gaagacgcca aaaacataaa gaaaggcccg gcgccattct atccgctgga agatggaacc      60
gctggagagc aactgcataa ggctatgaag agatacgccc tggttcctgg aacaattgct     120
tttacagatg cacatatcga ggtggacatc acttacgctg agtacttcga aatgtccgtt     180
cggttggcag aagctatgaa acgatatggg ctgaatacaa atcacagaat cgtcgtatgc     240
agtgaaaact ctcttcaatt ctttatgccg gtgttgggcg cgttatttat cggagttgca     300
gttgcgcccg cgaacgacat ttataatgaa cgtgaattgc tcaacagtat gggcatttcg     360
cagcctaccg tggtgttcgt ttccaaaaag gggttgcaaa aattttgaa cgtgcaaaaa      420 aagctcccaa tcatccaaaa aattattatc atggattcta aaacggatta ccagggattt     480
cagtcgatgt acacgttcgt cacatctcat ctacctcccg gttttaatga atacgatttt     540
gtgccagagt ccttcgatag ggacaagaca attgcactga tcatgaactc ctctggatct     600
actggtctgc ctaaaggtgt cgctctgcct catagaactg cctgcgtgag attctcgcat     660
gccagagatc ctattttggg caatcaaatc attccggata ctgcgatttt aagtgttgtt     720
ccattccatc acggttttgg aatgtttact acactcggat atttgatatg tggatttcga     780
gtcgtcttaa tgtatagatt tgaagaagag ctgtttctga ggagccttca ggattacaag     840
attcaaagtg cgctgctggt gccaacccta ttctccttct tcgccaaaag cactctgatt     900
gacaaatacg atttatctaa tttacacgaa attgcttctg gtggcgctcc cctctctaag     960
gaagtcgggg aagcggttgc caagaggttc catctgccag gtatcaggca aggatatggg    1020
ctcactgaga ctacatcagc tattctgatt acacccgagg gggatgataa accgggcgcg    1080
gtcggtaaag ttgttccatt ttttgaagcg aaggttgtgg atctggatac cgggaaaacg    1140
```

```
ctgggcgtta atcaaagagg cgaactgtgt gtgagaggtc ctatgattat gtccggttat    1200
gtaaacaatc cggaagcgac caacgccttg attgacaagg atggatggct acattctgga    1260
gacatagctt actgggacga agacgaacac ttcttcatcg ttgaccgcct gaagtctctg    1320
attaagtaca aaggctatca ggtggctccc gctgaattgg aat                      1363

<210> SEQ ID NO 9
<211> LENGTH: 726
<212> TYPE: DNA
<213> ORGANISM: tobacco etch virus

<400> SEQUENCE: 9
ggagaaagct tgtttaaggg accacgtgat tacaacccga tatcgagcac catttgtcat      60
ttgacgaatg aatctgatgg gcacacaaca tcgttgtatg gtattggatt tggtccttc     120 atcattacaa acaagcactt gtttagaaga ataatggaa cactgttggt ccaatcacta     180
catggtgtat tcaaggtcaa gaacaccacg actttgcaac aacacctcat tgatgggagg    240
gacatgataa ttattcgcat gcctaaggat ttcccaccat ttcctcaaaa gctgaaattt    300
agagagccac aaagggaaga gcgcatatgt cttgtgacaa ccaacttcca aactaagagc    360
atgtctagca tggtgtcaga cactagttgc acattcccctt catctgatgg catattctgg    420
aagcattgga ttcaaaccaa ggatgggcag tgtggcagtc cattagtatc aactagagat    480
gggttcattg ttggtataca ctcagcatcg aatttccacca acacaaacaa ttatttcaca    540
agcgtgccga aaaacttcat ggaattgttg acaaatcagg aggcgcagca gtgggttagt    600
ggttggcgat taaatgctga ctcagtattg tgggggggcc ataaagtttt catgagcaaa    660
cctgaagagc cttttcagcc agttaaggaa gcgactcaac tcatgaatga attggtgtac    720
tcgcaa                                                               726

<210> SEQ ID NO 10
<211> LENGTH: 7
<212> TYPE: PRT
<213> ORGANISM: Artificial
<220> FEATURE:
<223> OTHER INFORMATION: TEV recognition site

<400> SEQUENCE: 10

Glu Asn Leu Tyr Phe Gln Ser
 1               5

<210> SEQ ID NO 11
<211> LENGTH: 21
<212> TYPE: DNA
<213> ORGANISM: Artificial
<220> FEATURE:
<223> OTHER INFORMATION: recogniton site for TEV protease

<400> SEQUENCE: 11
gagaacctgt acttccagag c                                               21

<210> SEQ ID NO 12
<211> LENGTH: 7
<212> TYPE: PRT
<213> ORGANISM: artificial
<220> FEATURE:
<223> OTHER INFORMATION: recogniton site for TEV protease

<400> SEQUENCE: 12

Glu Asn Leu Tyr Phe Gln Val
 1               5
```

```
<210> SEQ ID NO 13
<211> LENGTH: 21
<212> TYPE: DNA
<213> ORGANISM: Artificial
<220> FEATURE:
<223> OTHER INFORMATION: DNA for cleavage site /V

<400> SEQUENCE: 13
gagaacctgt acttccaggt c                                              21

<210> SEQ ID NO 14
<211> LENGTH: 7
<212> TYPE: PRT
<213> ORGANISM: Artificial
<220> FEATURE:
<223> OTHER INFORMATION: recognition site

<400> SEQUENCE: 14

Glu Asn Leu Tyr Phe Gln Arg
1               5

<210> SEQ ID NO 15
<211> LENGTH: 21
<212> TYPE: DNA
<213> ORGANISM: Artificial
<220> FEATURE:
<223> OTHER INFORMATION: recognition site

<400> SEQUENCE: 15
gagaacctgt acttccagcg c                                              21
```